United States Patent
Keegan et al.

(10) Patent No.: US 12,429,485 B2
(45) Date of Patent: Sep. 30, 2025

(54) BIOMARKER PANELS FOR ON-TREATMENT PREDICTION OF RESPONSE TO IMMUNO-ONCOLOGY DRUGS

(71) Applicant: The Brigham and Women's Hospital, Inc., Boston, MA (US)

(72) Inventors: Alissa Keegan, Jamaica Plain, MA (US); David R. Walt, Boston, MA (US); Limor Cohen, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 487 days.

(21) Appl. No.: 17/413,383

(22) PCT Filed: Dec. 16, 2019

(86) PCT No.: PCT/US2019/066567
§ 371 (c)(1),
(2) Date: Jun. 11, 2021

(87) PCT Pub. No.: WO2020/124083
PCT Pub. Date: Jun. 18, 2020

(65) Prior Publication Data
US 2022/0011313 A1 Jan. 13, 2022

Related U.S. Application Data

(60) Provisional application No. 62/780,064, filed on Dec. 14, 2018.

(51) Int. Cl.
G01N 33/574 (2006.01)

(52) U.S. Cl.
CPC . *G01N 33/57488* (2013.01); *G01N 2333/521* (2013.01); *G01N 2333/525* (2013.01); *G01N 2333/54* (2013.01); *G01N 2333/5412* (2013.01); *G01N 2333/5421* (2013.01); *G01N 2333/5428* (2013.01); *G01N 2333/5443* (2013.01); *G01N 2333/545* (2013.01); *G01N 2333/55* (2013.01); *G01N 2333/57* (2013.01); *G01N 2333/7155* (2013.01)

(58) Field of Classification Search
None
See application file for complete search history.

(56) References Cited

U.S. PATENT DOCUMENTS

| | | | |
|---|---|---|---|
| 5,595,756 A | * | 1/1997 | Bally .......... A61K 9/1272 264/4.1 |
| 8,846,415 B2 | | 9/2014 | Duffy et al. |

FOREIGN PATENT DOCUMENTS

| | | |
|---|---|---|
| WO | WO 2011/109364 | 9/2011 |
| WO | WO 2016/057705 | 4/2016 |
| WO | WO 2008/049025 | 3/2018 |
| WO | WO 2018/102787 | 6/2018 |
| WO | WO 2018/225063 | 12/2018 |
| WO | WO-2018225063 A1 * | 12/2018 .............. A61P 35/00 |

OTHER PUBLICATIONS

The National Cancer Institute (downloaded from https://www.cancer.gov/about-cancer/treatment/types/immunotherapy/checkpoint-inhibitors on Oct. 30, 2023) (Year: 2023).*
Himmel et al, CMAJ Jun. 15, 2020;192:E651 (Year: 2020).*
Waiker et al (J Am Soc Nephrol. Jan. 2012; 23(1): 13-21) (Year: 2012).*
Brooks (Genome Res. Feb. 2012;22(2):183-7) (Year: 2012).*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000,10:398-400) (Year: 2000).*
Kulmanov et al (Bioinformatics, 34(4), 2018, 660-668) (Year: 2018).*
Vajdos et al. (J Mol Biol. Jul. 5, 2002;320(2):415-28) (Year: 2002).*
Brown et al. (J Immunol. May 1996; 156(9):3285-91) (Year: 1996).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
Mckeague et al (J Nucleic Acids. 2012;2012:748913. Epub Oct. 24, 2012) (Year: 2012).*
Guido et al (Curr Med Chem. 2008;15(1):37-46) (Year: 2008).*
Clark et al (J. Med. Chem., 2014, 57 (12), pp. 5023-5038) (Year: 2014).*
Rissin et al (Nat Biotechnol. Jun. 2010; 28(6): 595-599) (Year: 2010).*
Ellsworth PLoS One 12(9): e0183239 (Sep. 21, 2017) (Year: 2017).*
Smith et al (Am J Transl Res 2019;11(2):529-541) (Year: 2019).*
Heppner et al. (Cancer Metastasis Review 2:5-23; 1983) (Year: 1983).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042) (Year: 1997).*
Jain RK (Scientific American, Jul. 1994,58-65) (Year: 1994).*
Hogenesch et al (J Control Release. Dec. 10, 2012; 164(2): 183-186.) (Year: 2012).*
Hait (Nature Reviews/Drug Discovery, 2010, 9, pp. 253-254) (Year: 2010).*
Gravanis et al. (Chin Clin Oncol, 2014, 3, pp. 1-5) (Year: 2014).*
Beans (PNAS 2018; 115(50): 12539-12543) (Year: 2018).*
Adler et al., "Novel strategies and tools for enhanced sensitivity in routine biomolecule analytics," Current Pharmaceutical Analysis, Nov. 1, 2009, 5(4):390-407.

(Continued)

*Primary Examiner* — Brian Gangle
*Assistant Examiner* — Andrea K McCollum
(74) *Attorney, Agent, or Firm* — Fish & Richardson P.C.

(57) ABSTRACT

Biomarker panels for the prediction of patient response to immunotherapy, and methods of use thereof.

18 Claims, 20 Drawing Sheets

(56) References Cited

OTHER PUBLICATIONS

Akbay et al., "Activation of the PD-1 pathway contributes to immune escape in EGFR-driven lung tumors," Cancer Discovery, Dec. 1, 2013, 3(12):1355-63.

Akbay et al., "Interleukin-17A promotes lung tumor progression through neutrophil attraction to tumor sites and mediating resistance to PD-1 blockade," Journal of Thoracic Oncology, Aug. 1, 2017, 12(8):1268-79.

Aziz, "Measurement of circulating cytokines and immune-activation markers by multiplex technology in the clinical setting: what are we really measuring?," Forum on Immunopathological Diseases and Therapeutics, 2015, 6(1-2), 5 pages.

Buder-Bakhaya et al., "Biomarkers for clinical benefit of immune checkpoint inhibitor treatment—a review from the melanoma perspective and beyond," Frontiers in Immunology, Jun. 28, 2018, 9:1474.

Caetano et al., "IL6 blockade reprograms the lung tumor microenvironment to limit the development and progression of K-ras-mutant lung cancer," Cancer Research, Jun. 1, 2016, 76(11):3189-99.

Casaletto et al., "A comparison of biofluid cytokine markers across platform technologies: Correspondence or divergence?," Cytokine, Nov. 1, 2018, 111:481-9.

Chang et al., "Immuno-PCR: An ultrasensitive immunoassay for biomolecular detection," Analytica Chimica Acta, Mar. 3, 2016, 910:12-24.

Chen et al., "Analysis of immune signatures in longitudinal tumor samples yields insight into biomarkers of response and mechanisms of resistance to immune checkpoint blockade," Cancer Discovery, Aug. 1, 2016, 6(8):827-37.

Chen et al., "IL-6-stimulated CD11b+ CD14+ HLA-DR—myeloid-derived suppressor cells, are associated with progression and poor prognosis in squamous cell carcinoma of the esophagus," Oncotarget, Sep. 2014, 5(18):8716.

Chiou et al., "Pseudoprogression and immune-related response in solid tumors," Journal of Clinical Oncology, Nov. 1, 2015, 33(31):3541-3.

Churchman et al., "Multiplexing immunoassays for cytokine detection in the serum of patients with rheumatoid arthritis: lack of sensitivity and interference by rheumatoid factor," Clin Exp Rheumatol, Jul. 1, 2012, 30(4):534-42.

Cohen et al., "Impact of clinical sample handling and processing on ultra-low level measurements of plasma cytokines," Clinical Biochemistry, Mar. 1, 2019, 65, 14 pages.

Costa et al., "An analytical comparison of three immunoassay platforms for subpicomolar detection of protein biomarker GAD65," PloS one, Mar. 8, 2018, 13(3):e0193670.

Dabitao et al., "Multiplex measurement of proinflammatory cytokines in human serum: comparison of the Meso Scale Discovery electrochemiluminescence assay and the Cytometric Bead Array," Journal of Immunological Methods, Sep. 30, 2011, 372(1-2):71-7.

Das et al., "Combination therapy with anti-CTLA-4 and anti-PD-1 leads to distinct immunologic changes in vivo," The Journal of Immunology, Feb. 1, 2015, 194(3):950-9.

Eisenstein, "Making cancer immunotherapy a surer bet," Nature, Dec. 1, 2017, 552(7683):S72-3.

Fahey et al., "Need for an external proficiency testing program for cytokines, chemokines, and plasma markers of immune activation," Clinical Diagnostic Laboratory Immunology, Jul. 1, 2000, 7(4):540-8.

Fichorova et al., "Biological and technical variables affecting immunoassay recovery of cytokines from human serum and simulated vaginal fluid: a multicenter study," Analytical Chemistry, Jun. 15, 2008, 80(12):4741-51.

Gao et al., "Mutations in the EGFR kinase domain mediate STAT3 activation via IL-6 production in human lung adenocarcinomas," The Journal of Clinical Investigation, Dec. 3, 2007, 117(12):3846-56.

Greenwood et al., "Proximity assays for sensitive quantification of proteins," Biomolecular Detection and Quantification, Jun. 1, 2015, 4:10-6.

Holland et al., "Separation, banking, and quality control of peripheral blood mononuclear cells from whole blood of melanoma patients," Cell and Tissue Banking, Dec. 2018, 19(4):783-90.

Huang et al., "T-cell invigoration to tumour burden ratio associated with anti-PD-1 response," Nature, May 2017, 545(7652):60-5.

Koyama et al., "Adaptive resistance to therapeutic PD-1 blockade is associated with upregulation of alternative immune checkpoints," Nature Communications, Feb. 17, 2016, 7(1):1-9.

Li et al., "Abstract CT001; biomarkers of systemic inflammation associated to reduced clinical activity of atezolizumab monotherapy in patients with metastatic triple negative breast cancer," Proceedings: AACR Annual Meeting 2019, Atlanta, GA, Mar. 29-Apr. 3, 2019, 4 pages.

Li et al., "Inter-individual variability and genetic influences on cytokine responses to bacteria and fungi," Nature Medicine, Aug. 2016, 22(8):952-60.

Niemeyer et al., "Detecting antigens by quantitative immuno-PCR," Nature Protocols, Aug. 2007, 2(8):1918-30.

Ott et al., "Combination immunotherapy: a road map," Journal for Immunotherapy of Cancer, Dec. 2017, 5(1):1-5.

PCT International Preliminary Report on Patentability in International Appln. No. PCT/US2019/066567, dated Jun. 24, 2021, 11 pages.

PCT International Search Report and Written Opinion in International Appln. No. PCT/US2019/066567, dated Mar. 23, 2020, 13 pages.

Rebelatto et al., "Development of a programmed cell death ligand-1 immunohistochemical assay validated for analysis of non-small cell lung cancer and head and neck squamous cell carcinoma," Diagnostic Pathology, Dec. 2016, 11(1):1-4.

Rhodes et al., "C-reactive protein in rheumatology: biology and genetics," Nature Reviews Rheumatology, May 2011, 7(5):282-9.

Rissin et al., "Digital concentration readout of single enzyme molecules using femtoliter arrays and Poisson statistics," Nano Letters, Mar. 8, 2006, 6(3):520-3.

Rissin et al., "Digital readout of target binding with attomole detection limits via enzyme amplification in femtoliter arrays," Journal of the American Chemical Society, May 17, 2006, 128(19):6286-7.

Rissin et al., "Single-molecule enzyme-linked immunosorbent assay detects serum proteins at subfemtomolar concentrations," Nature biotechnology, Jun. 2010, 28(6):595, 20 pages.

Ryazantsev et al., "Immuno-PCR: achievements and perspectives," Biochemistry (Moscow), Dec. 2016, 81(13):1754-70.

Sano et al., "Immuno-PCR: very sensitive antigen detection by means of specific antibody-DNA conjugates," Science, Oct. 2, 1992, 258(5079):120-2.

Skalnikova et al., "Advances in proteomic techniques for cytokine analysis: focus on melanoma research," International Journal of Molecular Sciences, Dec. 2017, 18(12):2697.

Stenken et al., "Bioanalytical chemistry of cytokines—a review," Analytica Chimica Acta, Jan. 1, 2015, 853:95-115.

Tang et al., "Trial watch: the clinical trial landscape for PD1/PDL1 immune checkpoint inhibitors," Nature Reviews Drug Discovery, Dec. 1, 2018, 17(12):854-6.

Thavasu et al., "Measuring cytokine levels in blood. Importance of anticoagulants, processing, and storage conditions," Journal of Immunological Methods, Aug. 1, 1992, 153(1-2):115-24.

Todd et al., "Ultrasensitive flow-based immunoassays using single-molecule counting," Clinical Chemistry, Nov. 1, 2007, 53(11):1990-5.

Topalian et al., "Mechanism-driven biomarkers to guide immune checkpoint blockade in cancer therapy," Nature Reviews Cancer, May 2016, 16(5):275-87.

Tumeh et al., "PD-1 blockade induces responses by inhibiting adaptive immune resistance," Nature, Nov. 2014, 515(7528):568, 17 pages.

(56) References Cited

OTHER PUBLICATIONS

Vilain et al., "Dynamic changes in PD-L1 expression and immune infiltrates early during treatment predict response to PD-1 blockade in melanoma," Clinical Cancer Research, Sep. 1, 2017, 23(17):5024-33.

Weber et al., "Serum IL-6 and CRP as prognostic factors in melanoma patients receiving single agent and combination checkpoint inhibition," abstract, Journal of Clinical Oncology, May 2019, 37(15 supp) 100-100.

Wu et al., "Development and preliminary clinical validation of a high sensitivity assay for cardiac troponin using a capillary flow (single molecule) fluorescence detector," Clinical Chemistry, Nov. 1, 2006, 52(11):2157-9.

Wu et al., "Long-term measurements of human inflammatory cytokines reveal complex baseline variations between individuals," The American Journal of Pathology, Dec. 1, 2017, 187(12):2620-6.

Wu et al., "Single molecule array (Simoa) assay with optimal antibody pairs for cytokine detection in human serum samples," Analyst, Sep. 2015, 140(18):6277, 15 pages.

Yang et al., "Detection of plasma biomarkers using immunomagnetic reduction: a promising method for the early diagnosis of Alzheimer's disease," Neurology and Therapy, Jul. 2017, 6(1):37-56.

Yeung et al., "Evaluation of highly sensitive immunoassay technologies for quantitative measurements of sub-pg/mL levels of cytokines in human serum," Journal of Immunological Methods, Oct. 1, 2016. 437:53-63.

Yost et al., "Clonal replacement of tumor-specific T cells following PD-1 blockade," Nature Medicine, Aug. 2019, 25(8):1251-9.

Keegan et al., "Plasma IL-6 changes correlate to PD-1 inhibitor responses in NSCLC," Journal for Immunotherapy of Cancer, Oct. 2020;8(2), 8 pages.

* cited by examiner

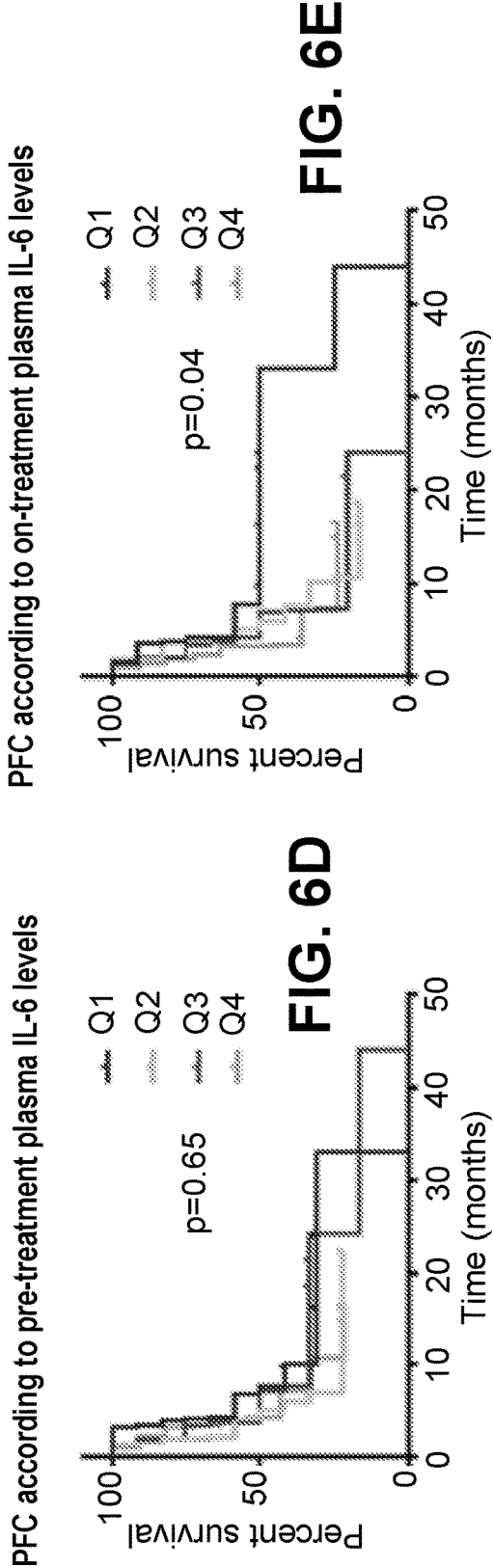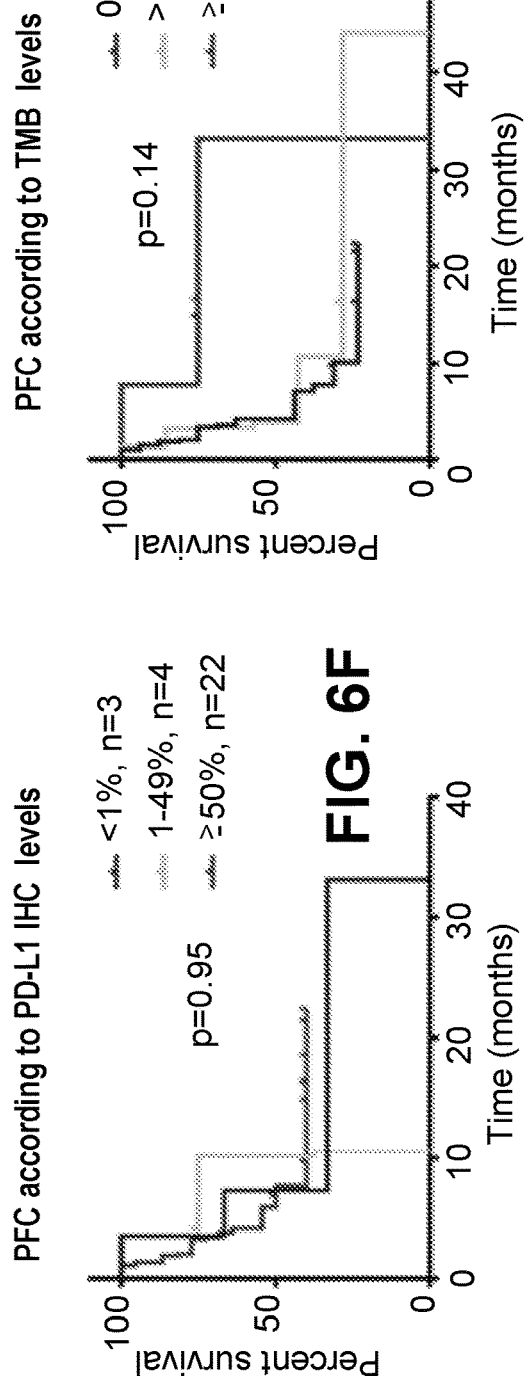

|  | Responders | Non-responders |
|---|---|---|
| Total number of patients | 6 | 6 |
| PFS months, range in months | 1 to 4 | 8 to 22 |
| Best Overall Response | | |
| PR | 5 | |
| SD | 1 | 4 |
| PD | | 2 |

FIG. 7A

BIOMARKER PANELS FOR ON-TREATMENT PREDICTION OF RESPONSE TO IMMUNO-ONCOLOGY DRUGS

CLAIM OF PRIORITY

This application is a § 371 National Stage Application of PCT/US2019/066567, filed Dec. 16, 2019, which claims priority to U.S. Patent Application Ser. No. 62/780,064, filed on Dec. 14, 2018, the entire contents of which are hereby incorporated by reference.

TECHNICAL FIELD

Described herein are biomarker panels for the prediction of patient response to immuno-oncology drugs, and methods of use thereof.

BACKGROUND

Inhibitors of the PD-1 pathway (PD-1i) are approved for many cancer types and hundreds of clinical trials are testing PD-1 blockade as a backbone therapy in combination with other agents. The realization of clinical immuno-oncology (I-O) presents unique challenges in patient selection, treatment sequencing, and response monitoring. In most cancer types, 10-50% of eligible patients will respond to PD-1i monotherapy (Topalian et al., Nat Rev Cancer. 2016; 16:275-87). The combination of approved I-O agents increases response rates but also the rates of toxicities including immune adverse effects (Ott et al., J Immunother Cancer. 2017; 5:16). While PD-L1 immunohistochemistry (IHC) and other pre-treatment biomarkers can enrich for patients more likely to respond to PD-1i monotherapy in the first-line setting, more than half of patients with high tumor PD-L1 still will not benefit (Topalian et al., supra).

SUMMARY

Described herein are panels of biomarkers, and method of using comparisons of changes in the levels of these biomarkers before and during (e.g., after at least one dose of) therapy to predict response and guide therapy selection. The panel of markers was identified through empiric testing of candidate markers in patient samples. The methods generally include comparing pre-treatment to levels after cycles 1 and 2 of therapy, as each individual has a different biomarker set-point (baseline). Without a comparison to an individual pre-treatment baseline, the on-treatment levels do not correlate with patient outcomes.

Thus, provided herein are methods method comprising: obtaining an initial (e.g., baseline) sample comprising blood, e.g., plasma or serum, from a subject who has cancer; administering to the subject at least one dose of an immune checkpoint inhibitor; obtaining a subsequent sample of blood from the subject; and measuring a level of one or more proteins listed in table A in the initial and subsequent samples.

In some embodiments, the methods further include comparing the levels of the one or more proteins in the initial and subsequent samples, and identifying a subject who has decreased levels of the one or more proteins in the subsequent sample as compared to the initial sample, and selecting and optionally administering further doses of the immune checkpoint inhibitor, or identifying a subject who has increased or no change in levels of the one or more proteins in the subsequence sample as compared to the initial sample, and selecting and optionally administering a therapy comprising further doses of the immune checkpoint inhibitor and at least one additional therapy, or a therapy not comprising the immune checkpoint inhibitor. Thus the methods can be used to select therapy, and optionally to treat subjects.

In some embodiments, the additional therapy or therapy not comprising the immune checkpoint inhibitor comprises administration of chemotherapy, radiotherapy, chemoradiotherapy, an immunotherapy not comprising the immune checkpoint inhibitor, and/or anti-angiogenic agents.

In some embodiments, the one or more proteins listed in table A comprise Interleukin 6 (IL-6) and C-reactive protein (CRP) or chemokine (C-X-C motif) ligand 10 (CXCL10), and optionally one or more of IL-10, IL-15, and IL-17A.

In some embodiments, the one or more proteins listed in table A comprise IL-6 and CRP; or the one or more proteins listed in table A comprise IL-6, IL-10, IL-15, IL-17A, CXCL10, and optionally IFNgamma.

In some embodiments, the one or more proteins listed in table A comprise CRP, IL-8, IL-15, IL-17A, IL-2 Receptor alpha, and soluble CD137.

In some embodiments, the one or more proteins further comprise soluble T cell immunoglobulin-3 (Tim-3), Lymphocyte activation gene-3 (Lag-3), or IL-2 Receptor alpha.

In some embodiments, measuring a level of one or more proteins listed in Table A comprises using an ultrasensitive protein detection technology, e.g., single molecule array digital ELISA (such as SIMOA).

In some embodiments, the immune checkpoint inhibitor is an inhibitor of PD-1 signalling, e.g., an antibody that binds to PD-1, CD40, or PD-L1; an inhibitor of CTLA4, e.g., an antibody to CTLA4; an inhibitor of Lag3, e.g., an antibody that binds to Lag3; or an inhibitor of Tim3, e.g., an antibody that binds to Tim3.

In some embodiments, the subject has a solid tumor. In some embodiments, the subject has lung cancer (e.g., non-small-cell lung cancer (NSCLC)), breast cancer, colorectal cancer, head and neck cancer, skin cancer (e.g., melanoma), or ovarian cancer. In some embodiments, the subject does not have melanoma or triple negative breast cancer.

In some embodiments, comparing the levels of the one or more proteins in the initial and subsequent samples comprises determining ratios or percentage change between the levels in the initial and subsequent samples.

In some embodiments, the methods further include determining an immuno-oncology (I-O) response score based on the levels, or ratios or percentage change between the levels in the initial and subsequent samples. In some embodiments, determining an I-O response score comprises applying principal component analysis or linear regression algorithm. In some embodiments, the methods include identifying a subject who has an I-O response score that is below a threshold, and selecting and optionally administering further doses of the immune checkpoint inhibitor, or identifying a subject who has an I-O response score that is below a threshold, and selecting and optionally administering a therapy comprising further doses of the immune checkpoint inhibitor and at least one additional therapy, or a therapy not comprising the immune checkpoint inhibitor.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6A-G. Outcomes by IL-6, PD-L1, and TMB levels. A and B. Percent of IL-6 change from pre- to on-treatment by 6 or 12 months durable clinical benefit cutoff $p=0.27$ and 0.08 by Mann-Whitney test. NDCB no durable clinical benefit. Patients with less than 6 months (n=1) or 12 months (n=3) of follow-up were excluded from this analysis. C. PFS by IL-6 change category (decreased, stable, increased) from pre- to on-treatment with PD-1 inhibitor. Only patients treated with pembrolizumab and with an on-treatment IL-6 level at the three-week timepoint after one dose of therapy are included in this analysis. $p=0.06$ by logrank test for trend. D and E. PFS by IL-6 levels at either pre-(D) or on-treatment (E) according to quartile (Q1 lowest to Q4 highest). $p>0.99$ comparing all quartiles by logrank test for trend. F and G. PFS by levels of PD-L1 IHC (F) and TMB (G). $p>0.99$ and $p=0.27$ comparing all levels by logrank test for trend.

FIGS. 7A-C. Cytokine changes in 12 pembrolizumab monotherapy patients with early radiologic responses: clear decrease for responders or increase for nonresponders in tumor burden at first scan and on-treatment timepoints three weeks after first dose of therapy. A. Table indicates patient outcomes across the response categories. B. Absolute concentrations of these cytokines from pre-treatment to three weeks after one cycle of pembrolizumab. Each line represents one patient with responders in grey and non-responders in black. The dotted horizontal line is the Simoa lower limit of quantitation (as shown in FIG. 5). The gray area represents the range of lower quantitation limits of other conventional immunoassays. C. Percentage change in the respective cytokine from pre-treatment to three weeks after first dose of therapy. Results from two independent experiments with different aliquots of the same plasma specimens are shown. Responder (R) Nonresponder (NR). **$p<0.01$, *$p<0.05$, ns not significant by Mann Whitney test.

DETAILED DESCRIPTION

Figure 1:
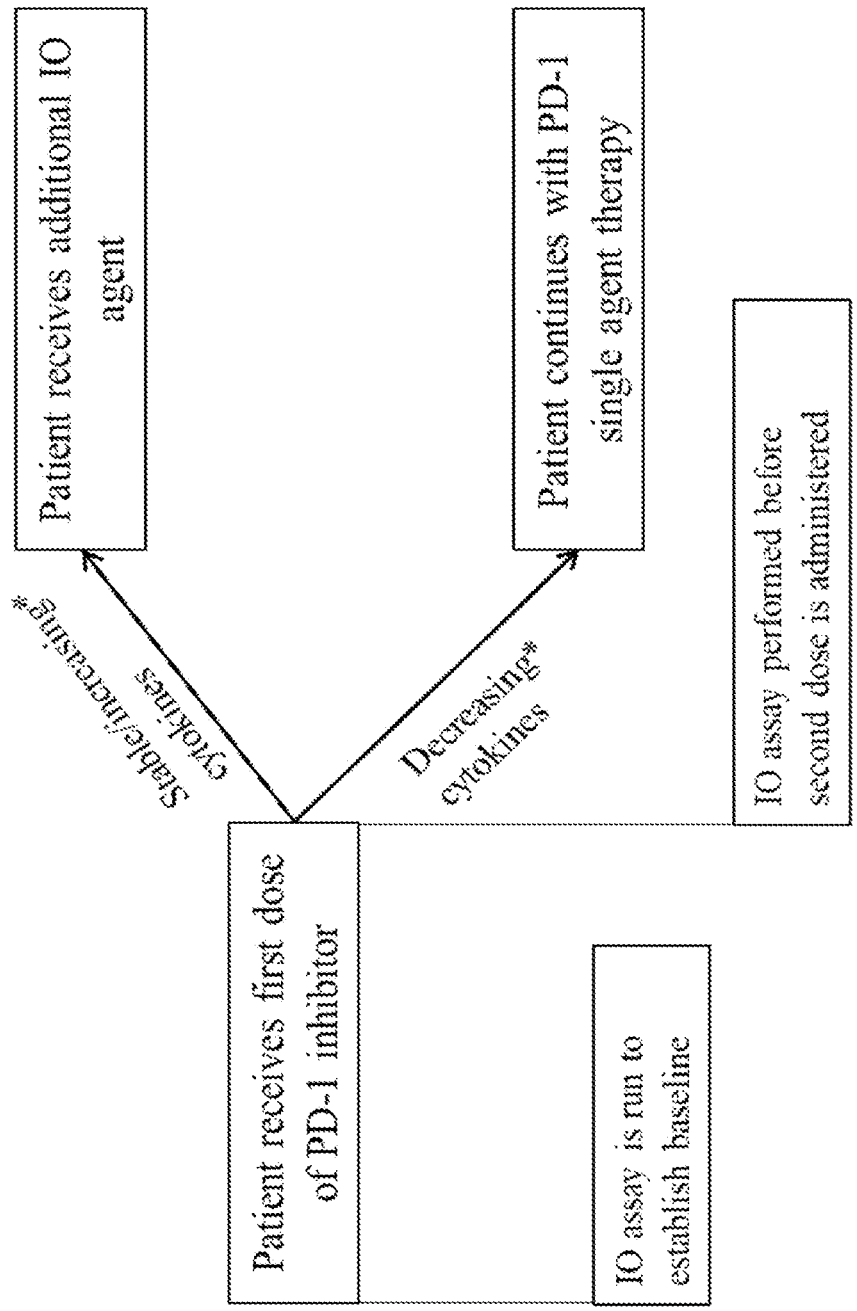
FIG. 1. Exemplary decision tree for allocation of PD-1 inhibitor combination therapy on the basis of an Immuno-oncology (I-O) cytokine panel as described herein. The I-O panel looks at changes in plasma cytokine levels. Generally, decreases across markers are associated with treatment response. The cut-off can be based on the number of markers and the magnitude of changes from baseline.

PD-1 pathway inhibitors are a groundbreaking class of immunotherapy cancer drugs and are effective in 10-50% of patients diagnosed with one of many types of metastatic cancer. A majority of patients, however, do not respond to these drugs and biomarkers for identifying responders and non-responders early in the course of treatment are needed to advance the field and improve the outcomes of patients receiving these agents. As opposed to conventional cytotoxic chemotherapy, response is difficult to evaluate by standard imaging and biomarkers may offer an improved indication of clinical benefit: for example, patients with immunological response can benefit from therapy for long durations even if imaging studies do not clearly show tumor shrinkage. Non-responders can forego unnecessary therapy and potentially be recruited to clinical trials testing novel combination immunotherapies.

With the oncoming wave of PD-1i combination therapeutic options (see, e.g., Tang et al., Nat Rev Drug Discov. 2018 Nov. 28; 17(12):854-855), there is a pressing clinical need for early identification of PD-1i-monotherapy unresponsive patients. 1-0 agents, by their indirect action of stimulating the innate and adaptive immune systems show prolonged kinetics of tumor regression, therefore standard radiologic measures are less reliable indicators of early on-treatment response (Ott et al., J Immunother Cancer. 2017; 5:16). CT scans can falsely overestimate disease burden in the presence of a brisk inflammatory response and a subset of responding patients will show long-term stabilization of disease, even after a mild initial increase in tumor burden (Chiou et al., J Clin Oncol Off J Am Soc Clin Oncol. 2015; 33:3541-3).

On-treatment biopsy studies demonstrate that responders show changes at the level of the tumor micro-environment (TME) with regard to cellular composition and gene expression profile (Chen et al., Cancer Discov. 2016; 6:827-37; Vilain et al., Clin Cancer Res. 2017 Sep. 1; 23(17):5024-5033). Compared to pre-treatment tissue analysis, early on-treatment tumor biopsy immunoprofiling shows greater accuracy for predicting response (Chen et al., supra; Vilain et al., supra). However, such biopsies are invasive and carry substantial risks to patients are not feasible in standard clinical care.

Some of the genes that are differentially expressed between responders and non-responders in on-treatment biopsies are soluble immunologic signaling molecules (cytokines and chemokines) (Chen et al., supra; Vilain et al., supra). However, a correlation to peripheral blood levels has not been shown, and many of these circulating molecules are below the limits of detection of conventional assays, especially in the absence of a systemic inflammatory response, as in PD1i blockade (Aziz, Forum Immunopathol Dis Ther. 2015; 6:19-22).

The present methods are based on the idea of "on-treatment diagnosis" disease characterization; as shown herein, every subject has a different disease state and immune constellation that affects likelihood of responding to immunotherapy treatment such that highly accurate pre-treatment response prediction based is not plausible. Once the subject has been given at least a single dose of the immunotherapy the present methods can be used to determine in a dynamic fashion, whether the anti-tumor immune response is mounted and the therapy is working. Described herein are plasma-based biomarker panels, measured at ultra-low concentrations from patient blood after as little as one dose of an immunotherapy (e.g., a PD-1 inhibitor), that can distinguish patients that respond to the immunotherapy from patients that do not respond. The panels can be used to generate a likelihood I-O response score by comparing patient baseline to on-treatment marker levels. In some embodiments, a specific data transformation is used to arrive at a prediction. This score can be used, optionally in combination with radiologic measures and disease markers such as tumor mutation burden and PD-L1 immunohistochemistry to guide I-O treatment decisions. In some embodiments, an oncologist submits plasma along with standard laboratory tests at least once in every cycle of therapy to arrive at a probability of ongoing response. Low probabilities could support adding a second I-O drug or discontinuing I-O therapy and changing to other agents. High I-O response scores can support a wait-and-watch approach until the radiologic response is clear. This assay can be used to personalize treatment sequencing for maximum safety and efficacy.

Detection Methods

The present methods make use of ultrasensitive protein detection technologies that can detect subpicogram/ml concentrations of proteins, e.g., in the pg/mL to fg/mL range. A number of such technologies are now available, including the single molecule array (SIMOA), a digital ELISA assay that achieves an average of 100-1000 times more sensitive protein quantification over existing methods (Rissin et al., Nat Biotechnol. 2010; 28:595-9; Wu et al., The Analyst. 2015; 140:6277-82). Other ultrasensitive assay methods that can be used include, e.g., the ERENNA Single Molecule Counting (SMC) assay (Singulex, Alameda, CA), which combines bead-based immunoassay with Single Molecule Counting detection methods (see, e.g., Wu et al., Clin Chem. 2006 November; 52(11):2157-9; Todd et al., Clin Chem. 2007 November; 53(11):1990-5); bead-based multianalyte profiling assay (e.g., LUMINEX (Biotechne) that uses color-coded superparamagnetic beads coated with analyte-specific antibodies, or Cytometric Bead Array (CBA, Becton, Dickinson and Company)); high performance el ectrochemiluminescence (e.g., ElectroChemiLuminescence ImmunoAssay (ECLIA) (Meso Scale Discovery); see, e.g., Dabitao et al., J Immunol Methods. 2011 Sep. 30; 372 (1-2): 71-7; Costa et al., PLoS One. 2018; 13 (3): e0193670); immunoPCR, which uses a detection antibody that is covalently conjugated to DNA and thus can be detected using quantitative PCR (Sano et al., Science. 1992 Oct. 2; 258(5079): 120-2; Adler et al., Curr. Pharm. Anal. 2009; 5:390-407; Ryazantsev et al., Biochemistry (Mosc). 2016 December; 81(13):1754-1770; Chang et al., Anal Chim Acta. 2016 Mar. 3; 910:12-24; methods of using immunoPCR to detect IL-6 in plasma are described in Niemeyer et al., Nat Protoc. 2007; 2(8):1918-30); proximity ligation/extension assay (PLA) or proximity extension assay (PEA), which typically use antibodies that bind to adjacent epitopes of target proteins and then to oligos, and detection is performed using RT-PCR (Greenwood et al., Biomol Detect Quantif. 2015 June; 4:10-6); immunomagnetic reduction (IMR) assay (e.g., the IMPERACER platform, Chimera Biotec GmbH), which uses capture antibodies immobilized on magnetic nanoparticles that become heavier and thus respond differently to magnetic field upon binding of an analyte to the nanoparticles (Yang et al., Neurol Ther. 2017 July; 6 (Suppl 1): 37-56; Yeung et al., J Immunol Methods. 2016 October; 437:53-63 used MIR to evaluate levels of IL-6, TNFα, IL-17a, IL-2). See also Fichorova et al., Anal Chem. 2008 Jun. 15; 80(12):4741-51; Skalnikova et al., Int J Mol Sci. 2017 December; 18(12):2697; Casletto et al., Cytokine, November 2018; 111:481-489.

Biomarker Panels

The combination of multiple markers in plasma-based immunotherapy response assessment will likely be necessary to focus specificity to the tumor-immune response. Cytokines are especially pleomorphic, working in networks that direct their local action. Candidate markers are preferably chosen to capture several cytokine networks in I-O response, with other classes of immune molecules such as chemokines and soluble immune receptors (e.g., soluble T cell immunoglobulin-3 (Tim-3), Lymphocyte activation gene-3 (Lag-3), soluble CD27). The preferred SIMOA assays use little plasma volume (from 5-100 μl, depending on the assay) and can be multiplexed; therefore, panels of 2, 3, 4, 5, 6, 7, 8, 9, 10, 12, or more markers that capture diverse mechanisms of the tumor-immune response can be used. In some embodiments, analytes that degrade >20%-40% after 4 hours at room temperature or that cannot be reliably and reproducibly detected will not be included. In some embodiments, the proteins include at least 2, 3, 4, 5, 6, 7, 8, 9, or all 10 of the markers listed in Table 1. Exemplary sequences for the proteins are provided in Table 1; if needed, antibodies to each protein are known in the art and/or can be obtained commercially or generated using known methods.

TABLE 1

Biomarkers

| Protein Biomarker | NCBI REF SEQ ID |
|---|---|
| Interleukin 6 (IL-6) | NP_000591.1; NP_001305024.1 |
| IL-8 | NP_000575.1 |
| IL-10 | NP_000563.1 |
| IL-15 | NP_000576.1 NP_751915.1 |
| IL-17A | NP_002181.1 |
| C-reactive protein (CRP) | NP_000558.2 |
| Chemokine (C-X-C motif) ligand 10 (CXCL10) | NP_001556.2 |
| CXCL13 | NP_006410.1 |
| Interferon gamma (IFNgamma) | NP_000610.2 |
| Soluble IL-2 Receptor alpha (CD25) | NP_000408.1 |
| T cell immunoglobulin mucin receptor 3 (Tim-3, also known as HAVCR2) | NP_116171.3 |
| Lymphocyte activating 3 (Lag-3) | NP_002277.4 |
| IL-1beta | NP_000567.1 |
| Vascular endothelial growth factor (VEGF) | NP_001165097.1 NP_001273973.1 |
| Transforming growth factor beta (TGFbeta) | NP_000651.3 |

In some embodiments, the panel includes two or more of IL-6, CRP, IL-10, IL-15, IL-17A, CXCL10, and optionally IFNgamma. In some embodiments, the panel includes, or also includes, one, two or more of CRP, IL-1beta, IL-6, IL-8, IL-15, and IL-17A. In some embodiments, the panel includes at least IL-6 and CRP or CXCL10, and optionally one or more of IL-10, IL-15, and IL-17A. In some embodiments, the panel includes one or more of soluble T cell immunoglobulin-3 (Tim-3), Lymphocyte activation gene-3 (Lag-3), or soluble IL-2 Receptor alpha.

Samples and Analysis

The present methods include capturing cytokines, chemokines, and soluble immune receptors emanating from the TME, from peripheral blood. Thus, the methods can include obtaining or providing a sample comprising peripheral blood from a subject who has cancer. The methods include obtaining a first or baseline sample from a subject prior to treatment with an immunotherapy, and then at least one subsequent sample after the subject has been administered one or more doses or cycles of the immunotherapy (for immune checkpoint inhibitors, one dose is one cycle). Known methods can be used to prepare the samples prior to analysis, e.g., directly from plasma or serum isolated by standard methods and frozen within 2-10 hours of blood draw (e.g., as described in Thavasu et al., J Immunol Methods. 1992 Aug. 30; 153 (1-2): 115-24). The sample can be obtained, e.g., 1, 2, 3, 5, 7, 10, 14, 21, or 28 days after the dose is administered.

Physiologically, many circulating cytokines and other immunologic molecules will vary diurnally and with common infectious exposures (i.e., viral infection, immunization); thus in some embodiments, multiple pre-treatment/baseline and post-treatment samples are taken from multiple patient time-points (Aziz, Forum Immunopathol Dis Ther. 2015; 6:19-22) and compared; in some embodiments, the pre-treatment/baseline and post-treatment samples are all taken at or about the same time of day (i.e., within 2-4 hours of the same time of day).

The methods include comparing the levels in the baseline or initial sample and the subsequent samples to detect changes within a subject; e.g., comparing the baseline level to the level obtained after administration of 1, 2, 3, 4, 5 or more doses. In general, the methods can include determining percentage change from baseline, or ratios, e.g., of post-treatment to pre-treatment levels.

The methods described herein can include calculating a score based on the percent change or ratios.

In some embodiments of the methods described herein, values representing the percent change or ratios can be summed to produce an "TO score" that can be compared to a reference TO score, wherein an TO cytokine score that is above the reference TO score indicates that the subject has stable or increasing levels of cytokines and is predicted to have a poor response or no response to the administered immunotherapy, and an TO score below the reference score indicates that the subject has decreasing levels of cytokines, or is predicted to have a positive response to the immunotherapy. As noted above, generally speaking, decreases across markers is associated with treatment response. The cut-off is based on the number of markers and the magnitude of the changes from baseline.

For example, in some embodiments, each of the evaluated proteins can be assigned a value (e.g., a value that represents the percent change or ratio of pre- and post-treatment levels). That value (optionally weighted to increase or decrease its effect on the final score) can be summed or otherwise analyzed to produce an TO score. One of skill in the art could optimize such a method to determine an optimal algorithm for determining an TO score, e.g., as described herein. Principal component analysis can be used, for example.

In some embodiments, the methods include applying an algorithm to concentration level data; e.g., a linear regression algorithm such as a rank-based linear regression algorithm as described herein. In some embodiments, the algorithm includes weighting coefficients for each of the protein markers. A linear regression model useful in the methods of determining an TO score can include the percent change or ratios of each protein and coefficients, or weights, for combining the percent changes or ratios. The coefficients can be calculated using a least-squares fit of the proposed model to a measure of immunotherapy response.

Reference Levels

In some embodiments of the methods described herein, the percent changes or ratios of the proteins can be compared individually to levels, ratios, or percent change in a reference subject or cohort of subjects. The reference levels, ratios, or percent change can represent levels, ratios, or percent change in a subject who is predicted to respond to the administered immunotherapy. Alternatively, reference levels, ratios, or percent change can represent levels, ratios, or percent change in a subject who is predicted to have a poor response or no response to the administered immunotherapy. In some embodiments, the reference levels, ratios, or percent change represent a threshold, and a level, percent change or ratio above the threshold reference level, ratio, or percent change indicates that the subject is predicted to have a poor response or no response to the administered immunotherapy, and a level, percent change or ratio below the threshold reference level indicates that the subject is predicted to have a positive response to the administered immunotherapy. In some embodiments, a decision tree such as that shown in FIG. 1 is followed. For example, in subjects who are predicted to respond positively to the immunotherapy, the methods can include administering further doses of the administered immunotherapy for those subjects, or selecting or recommending a treatment including the immunotherapy for those subjects. This has the benefit of avoiding the unnecessary administration of a second agent, which carries an increased risk of side effects.

In subjects who are predicted to respond poorly or not at all to the immunotherapy, the methods can include administering further doses of the administered immunotherapy with an additional (different) immunotherapy agent, or not including the administered immunotherapy to those subjects, or selecting or recommending a treatment that includes administering further doses of the administered immunotherapy with an additional (different) immunotherapy agent, or not including the administered immunotherapy to those subjects. This has the benefit of identifying non-responders identified early in the course of treatment and allowing allocation of maximally effective therapy to the highest risk group.

One of skill in the art will appreciate that references can be determined using known epidemiological and statistical methods, e.g., by determining an IO score in an appropriate cohort of subjects, e.g., subjects with the same type of cancer as the test subject and a known response to immunotherapy.

The predetermined level, ratio, or percent change can be a single cut-off (threshold) value, such as a median or mean, or a level, ratio, or percent change that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with likelihood of response (or non-response) to treatment in one defined group is a fold higher, or lower, (e.g., approximately 2-fold, 4-fold, 8-fold, 16-fold or more) than the likelihood of response in another defined group. It can be a range, for example, where a population of subjects (e.g., control subjects) is divided equally (or unequally) into groups, such as a low-probability of response group, a medium-probability of response group and a high-probability of response group, or into quartiles, the lowest quartile being subjects with the lowest probability of response and the highest quartile being subjects with the highest probability of response, or into n-quantiles (i.e., n regularly spaced intervals) the lowest of the n-quantiles being subjects with the lowest probability of response and the highest of the n-quantiles being subjects with the highest probability of response.

In some embodiments, the threshold or reference level, ratio, or percent change is zero.

Treatment

Also provided herein are methods that can be used to treat or determine treatment for a subject with cancer. In some embodiments, the methods can be used to predict response, select, administer, and/or monitor the efficacy of, a treatment, e.g., an immunotherapy, e.g., therapies that promote anti-cancer immunity (also referred to herein as immune-oncology treatments), including administering one or more of: dendritic cells or peptides with adjuvant, DNA-based vaccines, cytokines (e.g., IL-2), cyclophosphamide, anti-interleukin-2R immunotoxins, and/or antibodies such as anti-Tim3, anti-Lag3, anti-CD137, anti-PD1, anti-PDL1, or anti-CTLA-4; see, e.g., Krüger et al., "Immune based therapies in cancer," Histol Histopathol. 2007 June; 22(6):687-96; Eggermont et al., "Anti-CTLA-4 antibody adjuvant therapy in melanoma," Semin Oncol. 2010 October; 37(5): 455-9; Klinke D J 2nd, "A multiscale systems perspective on cancer, immunotherapy, and Interleukin-12," Mol Cancer. 2010 Sep. 15; 9:242; Alexandrescu et al., "Immunotherapy for melanoma: current status and perspectives," J Immunother. 2010 July-August; 33(6):570-90; Moschella et al., "Combination strategies for enhancing the efficacy of immunotherapy in cancer patients," Ann N Y Acad Sci. 2010 April; 1194:169-78; Ganesan and Bakhshi, "Systemic therapy for melanoma," Natl Med J India. 2010 January-February; 23(1):21-7; Golovina and Vonderheide, "Regulatory T cells: overcoming suppression of T-cell immunity," Cancer J. 2010 July-August; 16(4):342-7. In some embodiments, the immunotherapy includes administering a composition comprising tumor-pulsed dendritic cells, e.g., as described in WO2009/114547 and references cited therein, or Bispecific T cell engagers (BiTEs), e.g., as described in Huehls et al., Immunol Cell Biol. 2015 March; 93(3): 290-296.

In some embodiments, the initial treatment administered in the present methods is an immune checkpoint inhibitor, e.g., an inhibitor of PD-1 signaling, e.g., an antibody that binds to PD-1, CD40, or PD-L1, or an inhibitor of Tim3 or Lag3, e.g., an antibody that binds to Tim3 or Lag3.

Exemplary anti-PD-1 antibodies that can be used in the methods described herein include those that bind to human PD-1; an exemplary PD-1 protein sequence is provided at NCBI Accession No. NP_005009.2. Exemplary antibodies are described in U.S. Pat. Nos. 8,008,449; 9,073,994; and US20110271358, including PF-06801591, AMP-224, BGB-A317, BI 754091, JS001, MEDI0680, PDR001, REGN2810, SHR-1210, TSR-042, pembrolizumab, nivolumab, avelumab, pidilizumab, and atezolizumab.

Exemplary anti-CD40 antibodies that can be used in the methods described herein include those that bind to human CD40; exemplary CD40 protein precursor sequences are provided at NCBI Accession No. NP_001241.1, NP_690593.1, NP_001309351.1, NP_001309350.1 and NP_001289682.1. Exemplary antibodies include those described in WO2002/088186; WO2007/124299; WO2011/123489; WO2012/149356; WO2012/111762; WO2014/070934; US20130011405; US20070148163; US20040120948; US20030165499; and U.S. Pat. No. 8,591,900, including dacetuzumab, lucatumumab, bleselumab, teneliximab, ADC-1013, CP-870,893, Chi Lob 7/4, HCD122, SGN-4, SEA-CD40, BMS-986004, and APX005M. In some embodiments, the anti-CD40 antibody is a CD40 agonist, and not a CD40 antagonist.

Exemplary CTLA-4 antibodies that can be used in the methods described herein include those that bind to human CTLA-4; exemplary CTLA-4 protein sequences are provided at NCBI Acc No. NP_005205.2. Exemplary antibodies include those described in Tarhini and Iqbal, Onco Targets Ther. 3:15-25 (2010); Storz, MAbs. 2016 January; 8(1): 10-26; US2009025274; U.S. Pat. Nos. 7,605,238; 6,984,720; EP1212422; U.S. Pat. Nos. 5,811,097; 5,855, 887; 6,051,227; 6,682,736; EP1141028; and U.S. Pat. No. 7,741,345; and include ipilimumab, Tremelimumab, and EPR1476.

Exemplary anti-PD-L1 antibodies that can be used in the methods described herein include those that bind to human PD-L1; exemplary PD-L1 protein sequences are provided at NCBI Accession No. NP_001254635.1, NP_001300958.1, and NP_054862.1. Exemplary antibodies are described in US20170058033; WO2016/061142A1; WO2016/007235A1; WO2014/195852A1; and WO2013/079174A1, including BMS-936559 (MDX-1105), FAZ053, KN035, Atezolizumab (Tecentriq, MPDL3280A), Avelumab (Bavencio), and Durvalumab (Imfinzi, MEDI-4736).

Exemplary anti-Tim3 (also known as hepatitis A virus cellular receptor 2 or HAVCR2) antibodies that can be used in the methods described herein include those that bind to human Tim3; exemplary Tim3 sequences are provided at NCBI Accession No. NP_116171.3. Exemplary antibodies are described in WO2016071448; U.S. Pat. No. 8,552,156; and US PGPub. Nos. 20180298097; 20180251549; 20180230431; 20180072804; 20180016336; 20170313783; 20170114135; 20160257758; 20160257749; 20150086574; and 20130022623, and include LY3321367, DCB-8, MBG453 and TSR-022.

Exemplary anti-Lag3 antibodies that can be used in the methods described herein include those that bind to human Lag3; exemplary Lag3 sequences are provided at NCBI Accession No. NP_002277.4. Exemplary antibodies are described in Andrews et al., Immunol Rev. 2017 March; 276(1):80-96; Antoni et al., Am Soc Clin Oncol Educ Book. 2016; 35:e450-8; US PGPub. Nos. 20180326054; 20180251767; 20180230431; 20170334995; 20170290914; 20170101472; 20170022273; 20160303124, and include BMS-986016.

In subjects who are shown to have no change or an increase in the biomarkers described herein, the methods can include administering the initial immunotherapy with a second agent. The second agent can be, e.g., chemotherapy, radiotherapy, chemoradiotherapy and/or an anti-angiogenic agents (e.g., targeting VEGFA). Chemotherapy can be, e.g., using a cytotoxin or cytotoxic agent that is detrimental to cells. Examples include taxol, mitomycin, etoposide, tenoposide, vincristine, vinblastine, colchicin, doxorubicin, daunorubicin, mitoxantrone, mithramycin, actinomycin D, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). See, e.g., Johnson and Win, Oncoimmunology. 2018 Mar. 13; 7 (4):e1408744; Chowdhury et al., J Intern Med. 2018 February; 283(2):110-120; Tang et al., Nature Reviews Drug Discovery 17: 854-855 (2018).

Subjects

The methods can be to select a treatment, e.g., to select a treatment regime including immunotherapy for a subject who has a tumor, e.g., a solid tumor.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. In general, the methods described herein can be practiced on subjects with solid tumors.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers evaluated by the methods described herein include those that are particularly immunogenic, e.g., neuroblastoma, melanoma, and renal cell cancer, or any cancer where immunotherapy has been approved for treatment.

In some embodiments, cancers evaluated by the methods described herein include epithelial cancers, such as a lung cancer (e.g., non-small-cell lung cancer (NSCLC)), breast cancer, colorectal cancer, head and neck cancer, skin cancer (e.g., melanoma), or ovarian cancer. Epithelial malignancies are cancers that affect epithelial tissues.

In some embodiments, the cancer is a hematological cancer, e.g., lymphoma.

EXAMPLES

The invention is further described in the following examples, which do not limit the scope of the invention described in the claims.

Materials and Methods

The following materials and methods were used in the Examples below.

Sample Selection

In this retrospective study, pre-treatment and on-treatment plasma was collected at the Dana-Farber Cancer Institute between 2014 and 2018. Clinicopathologic data and treatment outcomes were collected from retrospective chart review and updated as of 6/15/19. Pre-treatment blood was drawn on the same day prior to first administration of PD-1 inhibitor. A total of 63 NSCLC patients were treated with either PD-(L)1 inhibitor monotherapy (n=43), PD-(L)1 inhibitor and other immunotherapy in a clinical trial setting (n=4), or with PD-1 inhibitor chemo-immunotherapy (n=16) in the first-line treatment setting. Patients treated with chemo-immunotherapy were excluded from the primary analysis for IL-6. Median PFS in the PD-(L)1 immunotherapy only group was 4.3 months and median PFS in the chemo-immunotherapy group was 6.4 months.

Sample Processing and Cytokine Measurements

Plasma was derived from whole blood EDTA specimens or as part of peripheral blood mononuclear cell collection as described previously (5, 18). The time between phlebotomy and plasma freeze did not exceed four hours. Single molecule array (Simoa) assays were performed as previously described with specifications provided (Tables A and B).

High sensitivity C-reactive protein (CRP) assays were performed on the Roche Cobas instrument in the clinical chemistry laboratory at Brigham and Women's Hospital.

TABLE A

Simoa assay specifications for all Simoa assays including number of steps, incubation times, enzyme and detection antibody concentrations, sample dilution factors, and reagent volumes.

| Target | Steps | Incubation Times (cadences) | Enzyme Concentration | Detection Antibody Concentration | Bead Volume |
|---|---|---|---|---|---|
| IL-1β | 2 | 47-7 | 150 pM | 0.3 µg/ml | 25 µl |
| IL-2 | 3 | 20-7-7 | 150 pM | 0.6 µg/ml | 25 µl |
| IL-6 | 3 | 20-7-7 | 150 pM | 0.3 µg/ml | 25 µl |
| IL-8 | 3 | 20-7-7 | 50 pM | 0.05 µg/ml | 25 µl |
| IL-10 | 3 | 20-7-7 | 150 pM | 0.3 µg/ml | 25 µl |
| IL-15 | 3 | 20-7-7 | 150 pM | 0.3 µg/ml | 25 µl |
| IL-17A | 3 | 20-7-7 | 150 pM | 0.3 µg/ml | 25 µl |
| IL-6Rα | 3 | 20-7-7 | 150 pM | 0.03 µg/ml | 25 µl |
| CXCL10 | 2 | 47-7 | 150 pM | 0.34 µg/ml | 25 µl |
| CXCL13 | 3 | 20-7-7 | 150 pM | 0.3 µg/ml | 25 µl |
| IFNγ | 2 | 47-7 | 150 pM | 0.3 µg/ml | 25 µl |
| TNFα | 2 | 47-7 | 150 pM | 0.22 µg/ml | 25 µl |

| Target | Sample Dilution Factor | Sample Volume | Detection Antibody Volume | Enzyme Volume |
|---|---|---|---|---|
| IL-1β | 4 | 170 µl | 20 µl | 100 µl |
| IL-2 | 4 | 120 µl | 100 µl | 100 µl |
| IL-6 | 4 | 100 µl | 100 µl | 100 µl |
| IL-8 | 6 | 100 µl | 100 µl | 100 µl |
| IL-10 | 4 | 100 µl | 100 µl | 100 µl |
| IL-15 | 4 | 100 µl | 100 µl | 100 µl |
| IL-17A | 4 | 100 µl | 100 µl | 100 µl |
| IL-6Rα | 100 | 100 µl | 100 µl | 100 µl |
| CXCL10 | 8 | 100 µl | 20 µl | 100 µl |
| CXCL13 | 6 | 100 µl | 100 µl | 100 µl |
| IFNγ | 4 | 100 µl | 20 µl | 100 µl |
| TNFα | 4 | 100 µl | 20 µl | 100 µl |

Data Analysis

Figure 5:
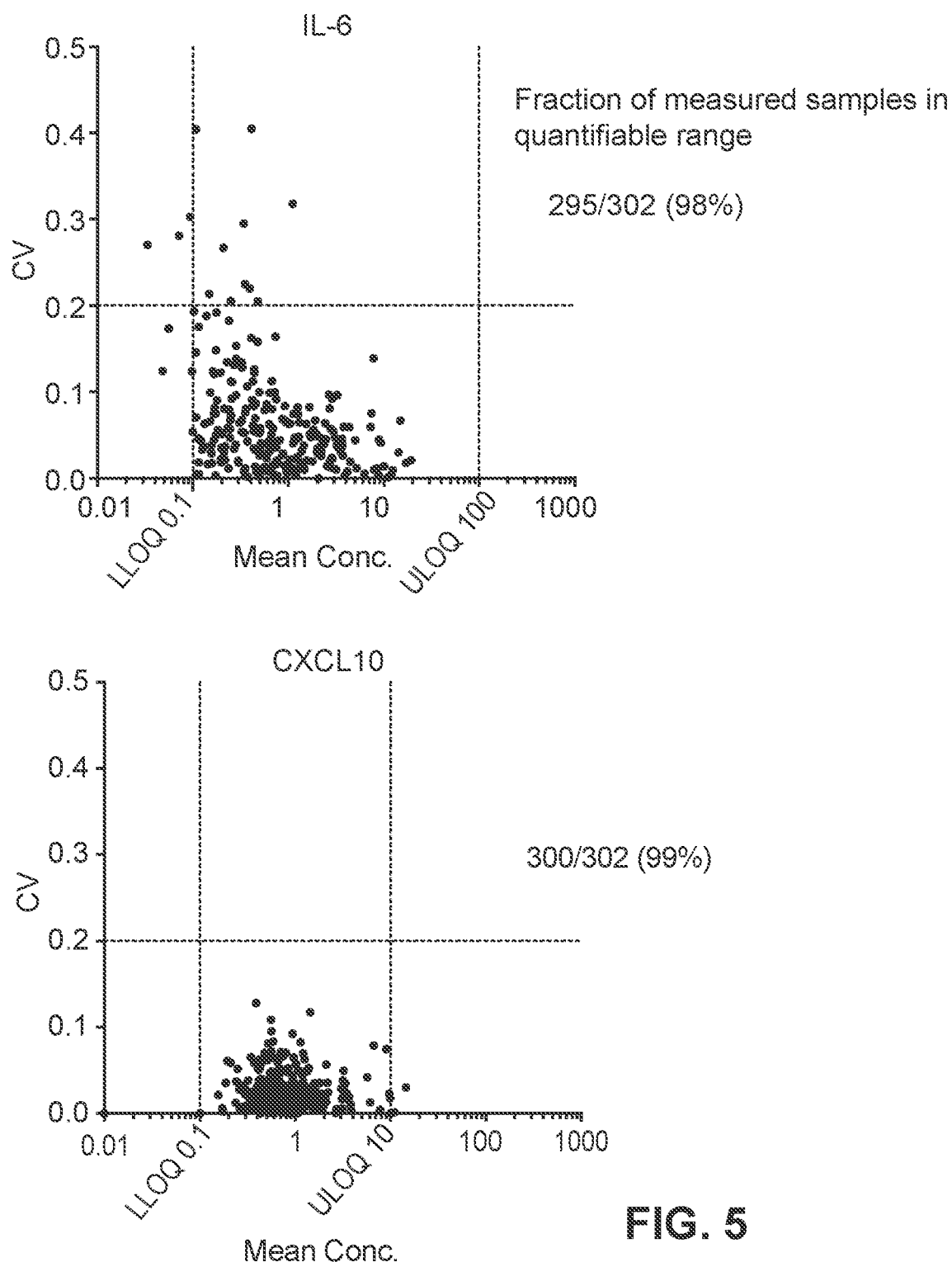
FIG. 5. Lower and upper limits of quantitation (vertical lines) were derived from calibrators and sample concentrations with less than 20% coefficient of variation (horizontal line). The fraction of plasma samples (including both pre- and on-treatment samples) is this reportable measuring range are reported in the top right quadrant. All cytokine levels below the LLOQ or above the ULOQ were set to the respective limit for the downstream analysis.
Figure 5:
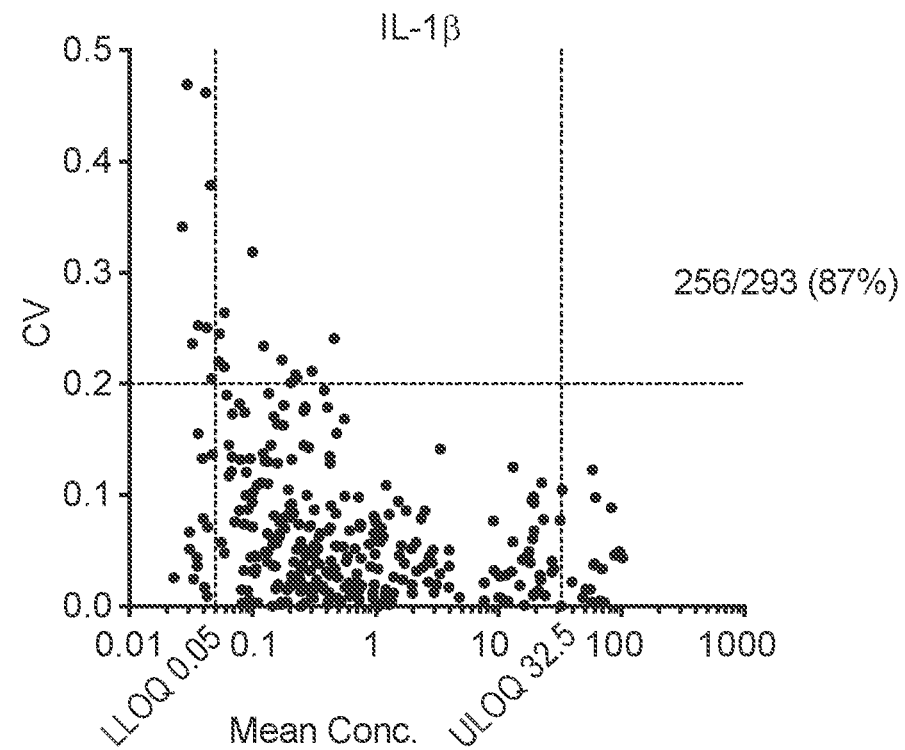
Figure 5:
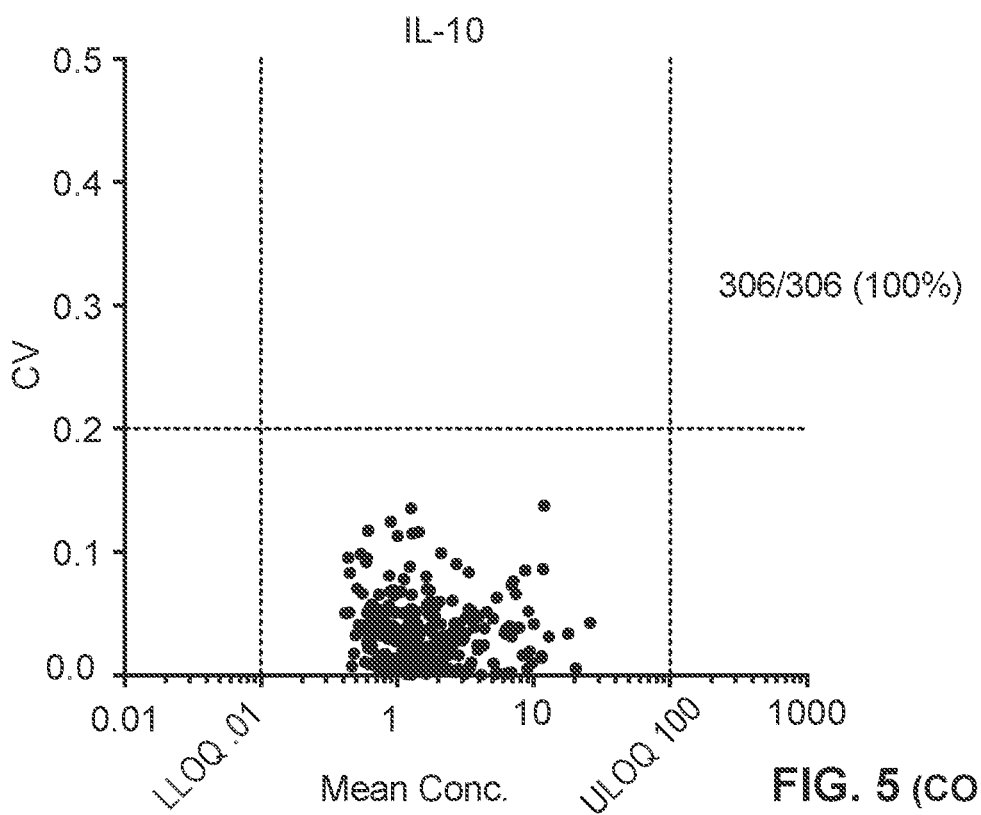
Figure 5:
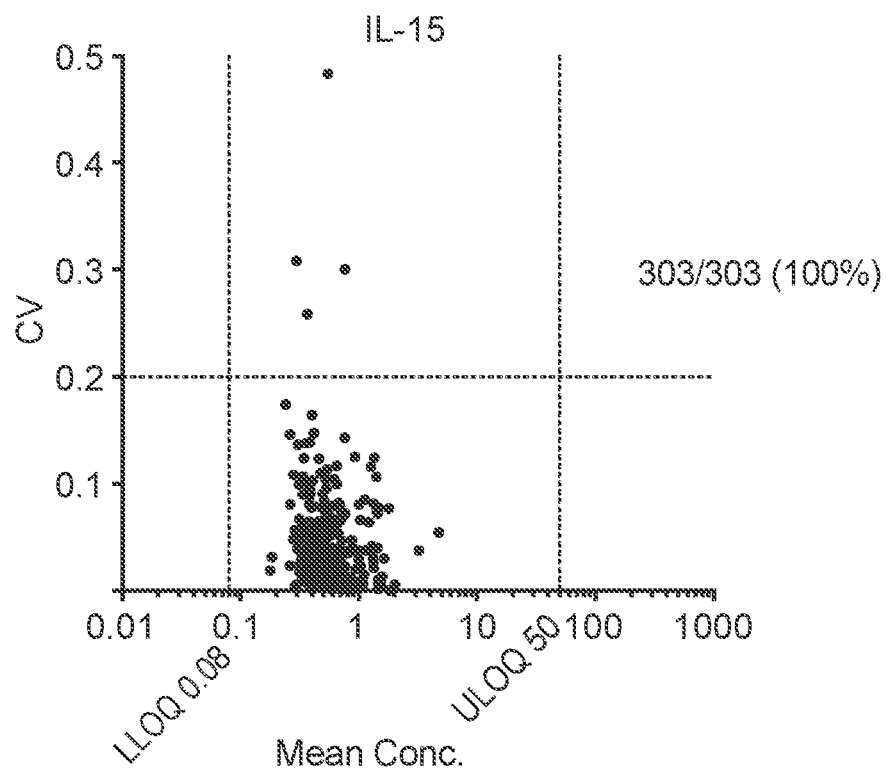
Figure 5:
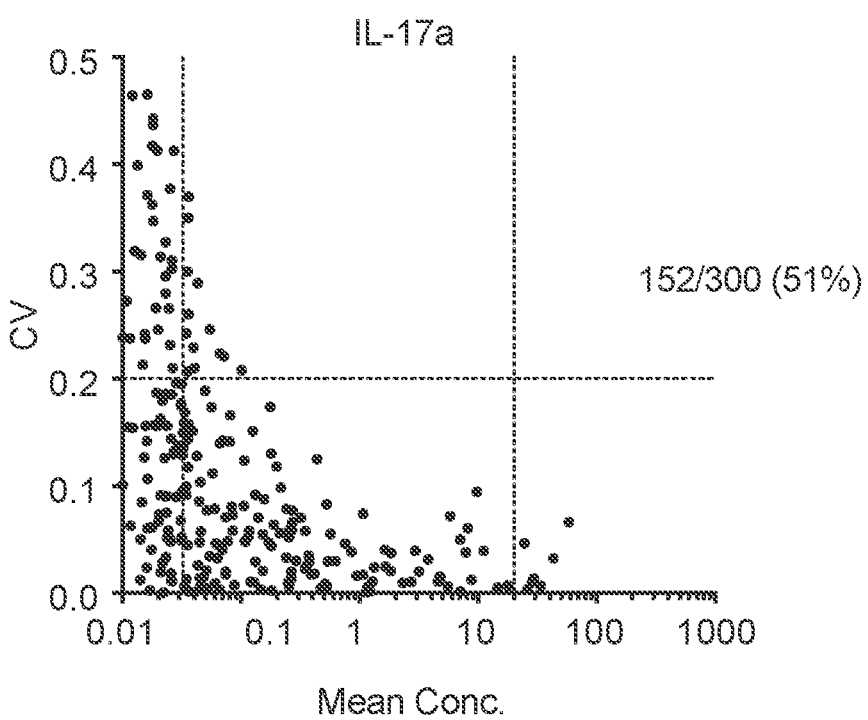

All samples were measured in duplicate and averaged. Lower and upper limits of quantitation (FIG. 5) were derived from calibrators and sample concentrations with less than 20% coefficient of variation. Cytokine levels outside the lower or upper limits of quantitation were set to the respective limit. The cutoff for significant change in IL-6 was derived from empiric validation of the collection protocol. It was observed that in the time window from two to six hours from blood collection, IL-6 consistently decreased by an average of 15% and a maximum of 30% in 19 unique samples across a wide concentration range (5). Therefore, at or above a conservative cutoff of 40%, changes between pre-treatment to on-treatment levels from the same patient were considered to represent significant biologic variation and not potential artifact from in vitro decreases. In vitro decreases in IL-6 could be mitigated by sample refrigeration and rapid processing, however, for the purposes of this exploratory study, standard clinical laboratory workflows were utilized. Data were analyzed and graphed in GraphPad Prism (San Diego, CA).

TABLE B

List of capture and detection antibodies and protein standards used for all Simoa assays.

| Target | Capture Antibody | Detection Antibody | Protein Standard |
|---|---|---|---|
| IL-1β | Biolegend 508202 | Biolegend 511703 | R&D Systems 201-LB |
| IL-2 | R&D Systems MAB602 | R&D Systems MAB202 | R&D Systems 202-IL |
| IL-6 | R&D Systems MAB206 | R&D Systems BAF206 | R&D Systems 206-IL |
| IL-8 | BD Biosciences 554716 | BD Biosciences 554718 | R&D Systems 208IL |
| IL-10 | BioLegend 506802 | BioLegend 501501 | R&D Systems 217-IL |
| IL-15 | R&D Systems MAB647 | R&D Systems BAM247 | R&D Systems 247-ILB |
| IL-17A | R&D Systems MAB317 | R&D Systems BAF317 | Biolegend 570509 |
| IL-6Rα | R&D Systems DY227 | R&D Systems DY227 | R&D Systems DY227 |
| CXCL10 | BioLegend 524402 | BioLegend 519403 | R&D Systems 266-IP |
| CXCL13 | R&D Systems DY801 | R&D Systems DY801 | R&D Systems DY801 |
| IFNγ | BioLegend 507502 | R&D Systems MAB285 | R&D Systems 285-IF |
| TNFα | R&D Systems MAB610 | AbCam ab9635 | R&D Systems 210-TA |

Example 1. On Therapy Plasma Biomarker Changes Correlate to PD-1 Inhibitor Responses in NSCLC Cytokines are immunologic signaling proteins that act primarily at the local cellular level but are also released into circulation, where most are present at very low concentrations (1). Across malignancies, the response to ICB is accompanied by changes in cytokine gene expression and cellular composition in the tumor microenvironment (TME) (2). These immunologic changes reflect the direct mechanism of PD-(L)1 blockade and precede changes in tumor burden. Compared to the pre-treatment response biomarkers, tissue PD-L1 levels and tumor mutation burden, on-treatment changes in tumor microenvironment gene expression more accurately reflect long term responses (3, 4). Many of these changes implicate soluble proteins, cytokines and chemokines, that could enter systemic circulation and represent attractive targets for minimally-invasive response assessment.

Single molecule array (Simoa), a new technology quantifying protein levels down to attomolar concentrations, enables accurate quantification of serum and plasma cytokine levels (5-7). Here we apply this technology to the development of immune checkpoint blockade (ICB) response biomarkers. Recent studies with Simoa have begun to better characterize the physiologic and laboratory variation in blood cytokine levels. Even amongst healthy adults, the baseline levels of serum cytokines have been shown to vary by as much as $10^4$ in concentration (8). The intraindividual variation was small, when samples were drawn weekly at the same time of day, over many months. For individuals who became ill with viral infection, the cytokine levels peaked around the time of viral illness symptoms but returned back to baseline (8). These observations suggest that each individual has a cytokine setpoint, potentially contributed to by genetic variants affecting circulating cytokine levels (9), and that short-term perturbations due to either disease, vaccine, or medication lead to temporary deviations from the setpoint. Another study characterized the in vitro stability of plasma cytokines (5). Even when cytokines are found at sub-pg/mL concentration, they could be accurately measured from clinical material stored at room temperature, with minor decreases over a four to six hour time frame between collection and freeze. These findings suggest biological relevance in monitoring changes in an individual's plasma cytokine levels.

In this study, we investigated plasma changes in 12 cytokines in relation to responses to PD-(L)1 blockade in NSCLC patients. We also explored the association of longitudinal changes in six cytokines with immune-related adverse effects in three patients.

Results

Figure 2A:
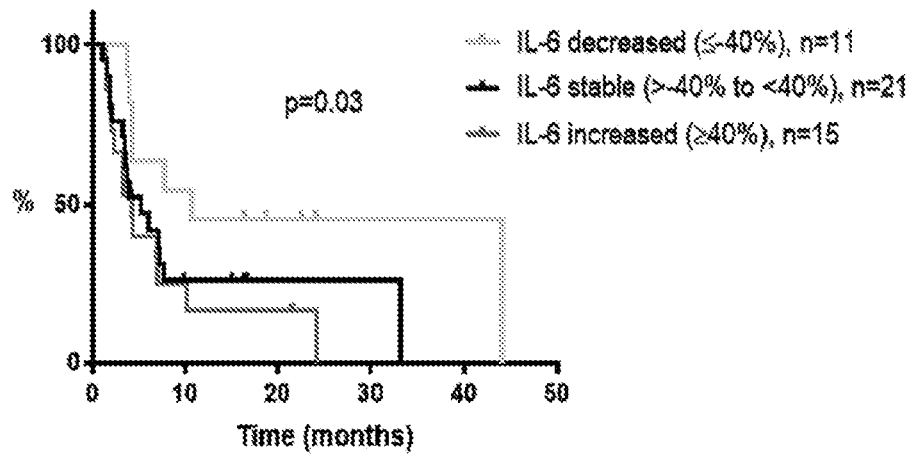
FIGS. 2A-B. Outcomes by IL-6 change A. PFS by IL-6 change category (decreased, stable, or increased) from pre- to on-treatment with PD-1 inhibitor. Patients treated with chemotherapy were excluded from this analysis. $p=0.03$ by logrank test for trend. B. Percent of IL-6 change from pre- to on-treatment by best overall response category. $p=0.01$ by Kruskall-Wallis test.
Figure 2B:
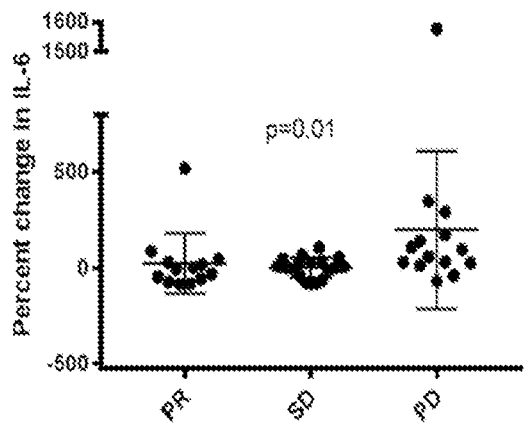
Figure 6A:
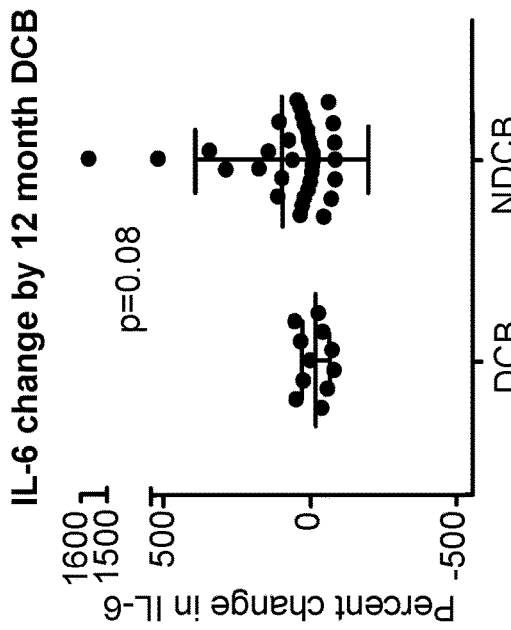
Figure 6B:
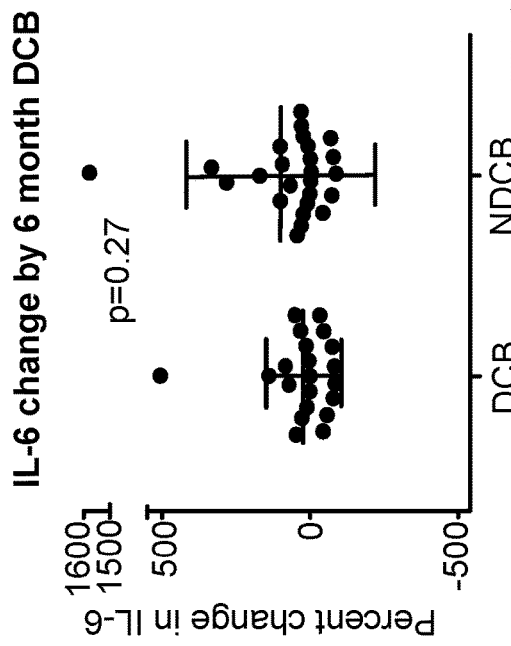
Figure 6C:
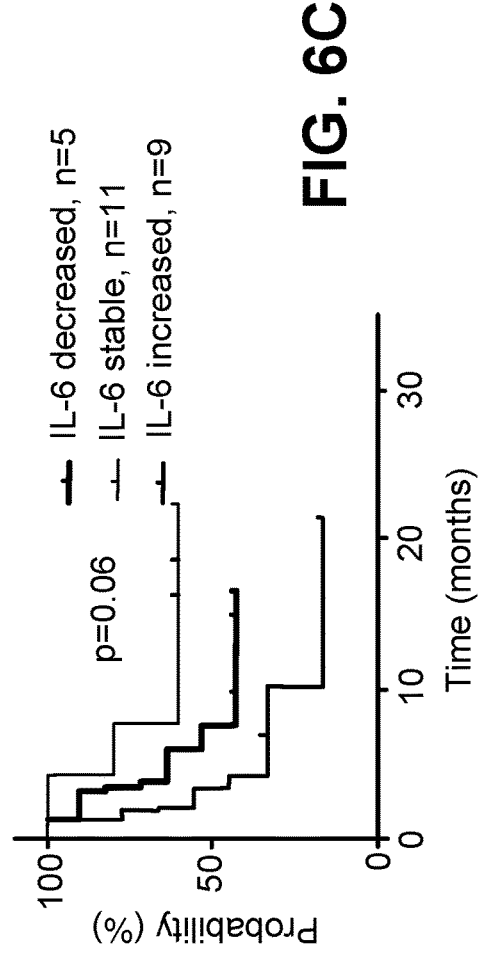

We identified 47 patients with metastatic NSCLC treated with inhibitors of the PD-1 pathway (Table 1); 33 received pembrolizumab, ten received nivolumab, and four received other agents. All patients had plasma collected immediately before first infusion of PD-(L)1 inhibitor and at on-treatment timepoints between 17 and 196 days on treatment. The majority of patients had adenocarcinoma (83%) and history of smoking (94%). Approximately half of patients received pembrolizumab monotherapy in the first-line setting (53%) and PD-L1 IHC levels were a median of 70% positive.

according to best overall response (BOR) category, with more increases in IL-6 in the progressive disease category (p=0.01, FIG. 2). There was no significant difference in IL-6 changes between patients with and without durable clinical benefit of either 6 or 12 months (FIG. 6A, 2B). The subset of patients (n=25) treated with first-line pembrolizumab monotherapy with an on-treatment sample collected three weeks after the first dose of therapy did not show significant differences in PFS according to IL-6 change category, however, IL-6 decreases trended towards longer PFS (FIG. 6C). Pre-treatment IL-6 levels ranged from 0.58 to 68 pg/mL and did not correlate with PFS (FIG. 6D). On-treatment IL-6 levels ranged from 0.60 to 78 pg/mL and only the quartile of patients with the lowest levels tended to have a longer PFS (FIG. 6E). For patients in this cohort with available data, there was no significant association of PFS with either PD-L1 levels (n=29) or tumor mutation burden (TMB, n=27) (FIG. 6F, 2G). Patients with IL-6 decreases were younger (p=0.046) and had higher PD-L1 IHC levels (p=0.003) and higher TMB (p=0.02) (Table 1, Kruskall-Wallis, age and TMB, and Fisher exact test, PD-L1).

In addition to IL-6, we developed ten other ultrasensitive Simoa plasma cytokine assays and one assay for the soluble IL-6 receptor, a subunit. We then applied the battery of assays on a subset of the cohort: twelve pembrolizumab

TABLE 1

Clinicopathological characteristics and outcomes according to percent change in IL-6 with start of PD-1 inhibitor

|  | IL-6 decreased | IL-6 stable | IL-6 increased | All patients |
| --- | --- | --- | --- | --- |
| Number of patients (%) | 11 (23) | 21 (44) | 15 (32) | 47 |
| Interval between pre and mid-treatment plasma draw in days, median (range) | 28 (17-196) | 22 (20-126) | 28 (21-70) | 28 (17-196) |
| Age at treatment start, median (range) | 63 (46-62) | 73 (50-89) | 72 (52-80) | 66 (46-89) |
| Male Sex, number (%) | 6 (54) | 5 (24) | 5 (33) | 16 (34) |
| Performance status 0/1/2 | 3/8/0 | 4/14/3 | 3/11/1 | 10/33/4 |
| Smoking history, number (%) | 10 (91) | 20 (95) | 14 (93) | 44 (94) |
| Histology, number (%) |  |  |  |  |
| Adenocarcinoma | 10 (91) | 18 (86) | 11 (73) | 39 (83) |
| Squamous | 1 (9) | 3 (14) | 4 (27) | 8 (17) |
| TMB, median mut/MB (range) | 15 (8-27) | 8 (4-42) | 5 (2-18) | 8 (2-42) |
| Patients with data not available (%) | 4 (36) | 10 (48) | 6 (40) | 20 (42) |
| PD-L1%, median (range) | 85 (30-95) | 50 (0-95) | 70 (5-80) | 70 (0-95) |
| Patients with data not available (%) | 5 (45) | 7 (79) | 6 (40) | 19 (40) |
| Treatment type |  |  |  |  |
| Pembrolizumab | 6 (54) | 15 (71) | 12 (80) | 33 (70) |
| Nivolumab | 4 (36) | 5 (24) | 1 (7) | 10 (21) |
| Atezolizumab | 1 (9) | 0 | 2 (13) | 3 (6) |
| Durvalumab | 0 | 1 (5) | 0 | 1 (2) |
| Line of therapy, median (range) | 2 (1-6) | 1 (1-5) | 1 (1-3) | 1 (1-6) |
| PFS in months, median (range) | 11 (4-44) | 5 (1-33) | 4 (1-24) | 4 (1-44) |
| Patients without progression at 12 months/patients with either progression or at least 12 months of follow-up (%) | 5/11 (45) | 4/19 (21) | 2/14 (14) | 11/44 (25) |

Figure 3A:
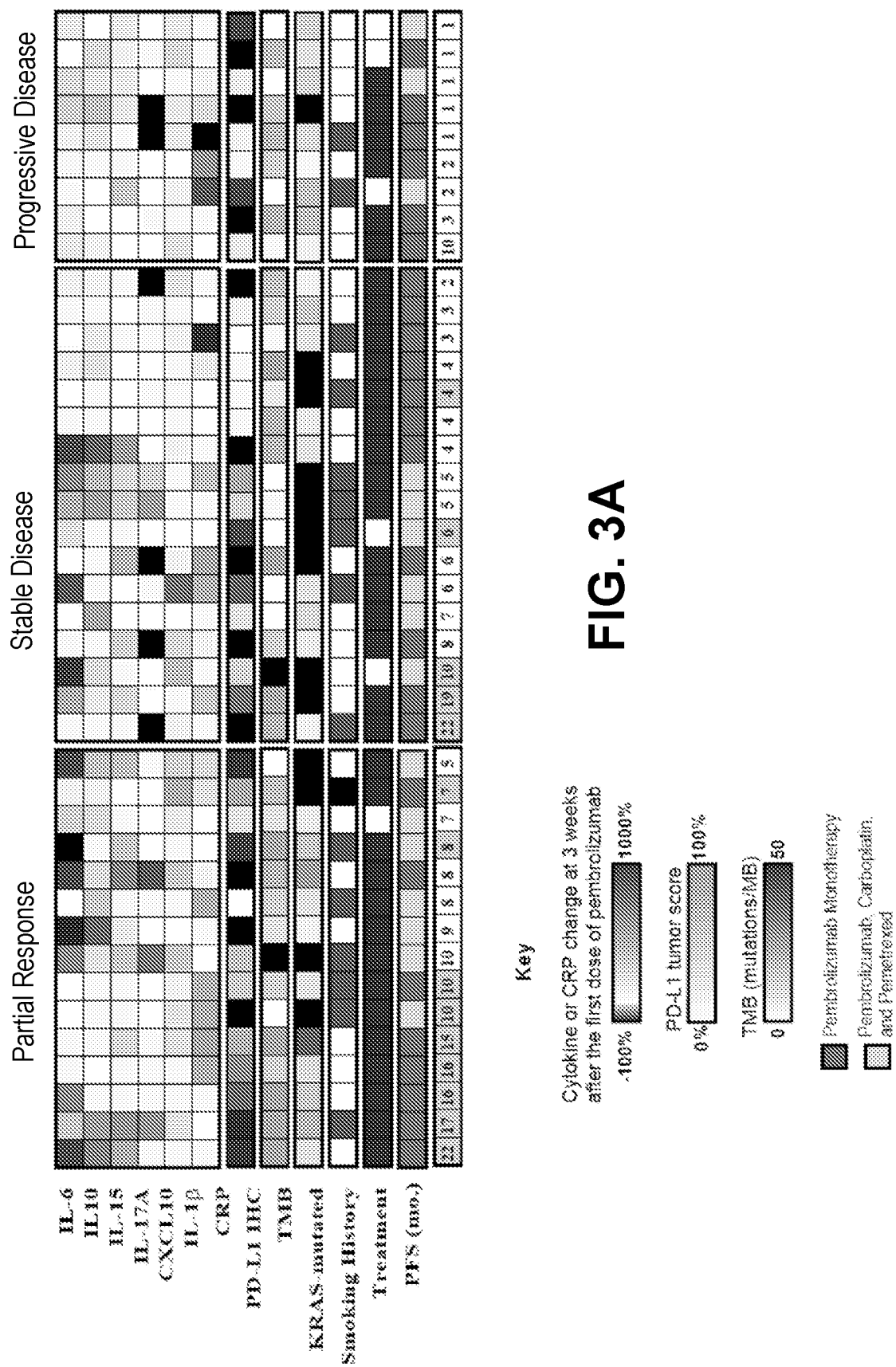
FIGS. 3A-E. All cytokines and CRP percent changes three weeks after one dose of pembrolizumab (monotherapy or combination chemotherapy) in relation to other clinicopathologic features and treatment outcomes. A. Heatmap illustrating cytokine changes in relation to other clinicopathologic correlates and outcomes. Each column represents one patient. Columns are organized by best overall response category and PFS. Black squares indicate missing data. White squares indicate KRAS non-mutated and no smoking history in the respective rows. Pink squares indicates PFS data was censored and patients did not progress by the analysis cutoff date. B. Comparison of IL-6 and CRP percent changes. C-E. PFS by CRP levels at either pre-(C), on-treatment (D), or percent change (E) according to quartile (C, D) or change category. $p=0.42$, $p<0.01$, $p<0.01$ by logrank test for trend.
Figure 3C:
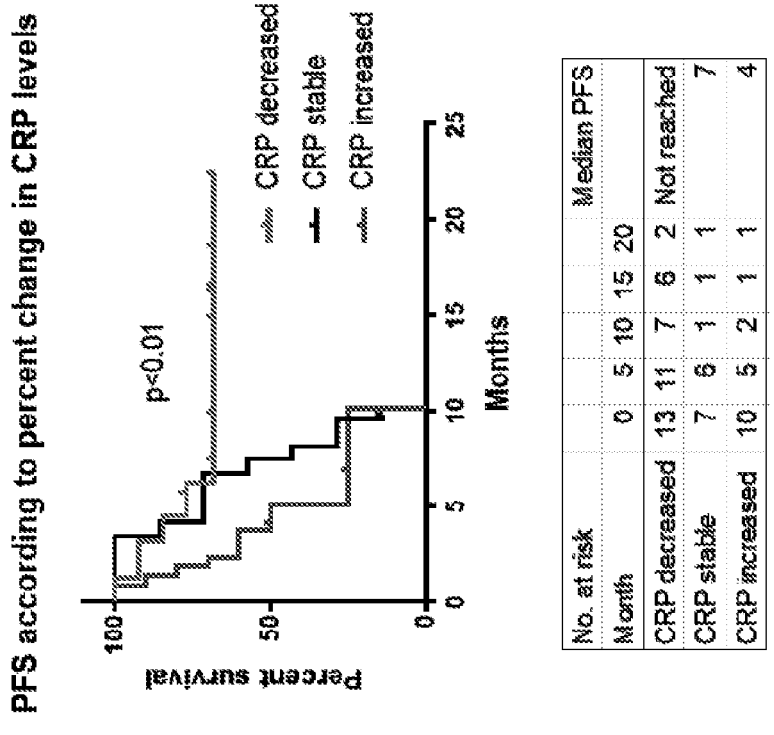
Figure 3B:
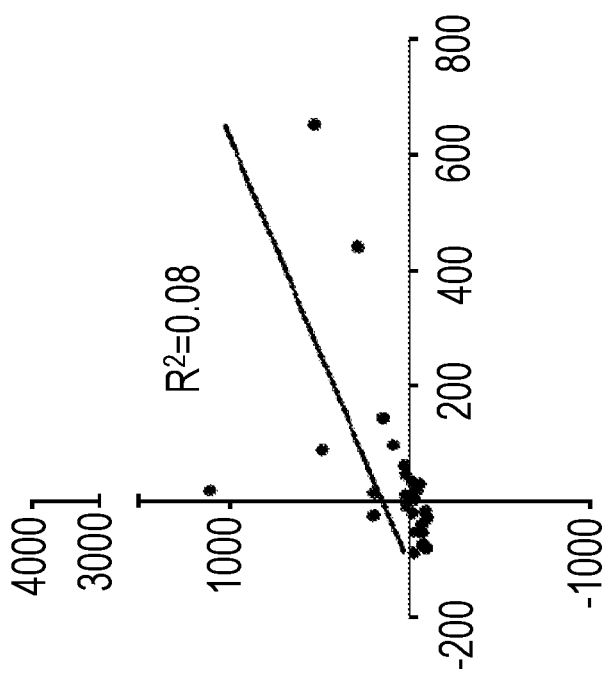
Figure 3D:
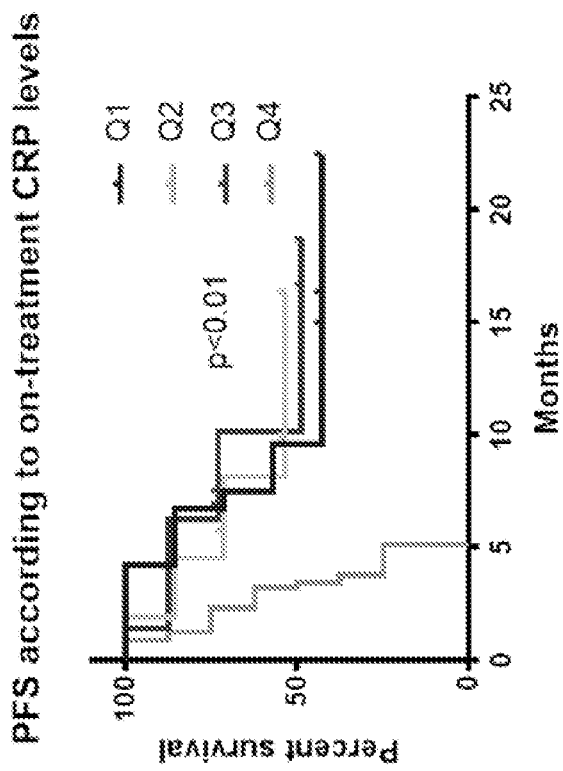
Figure 3E:
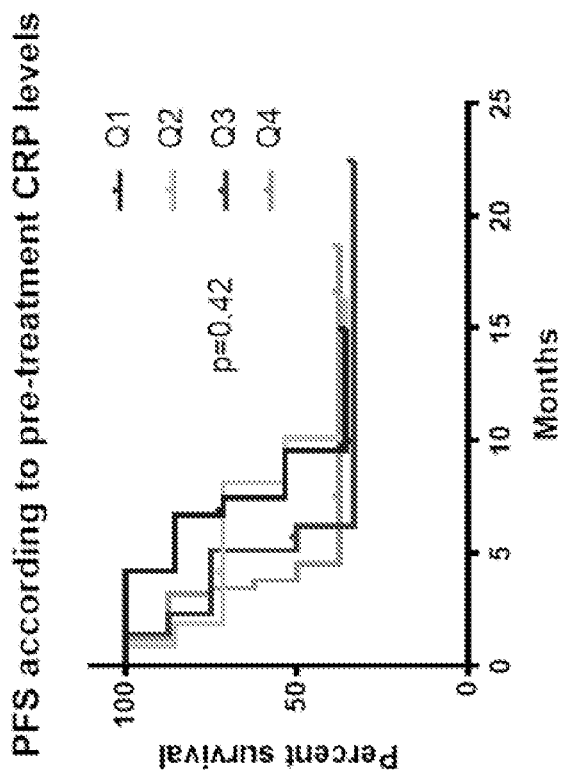
Figure 4A:
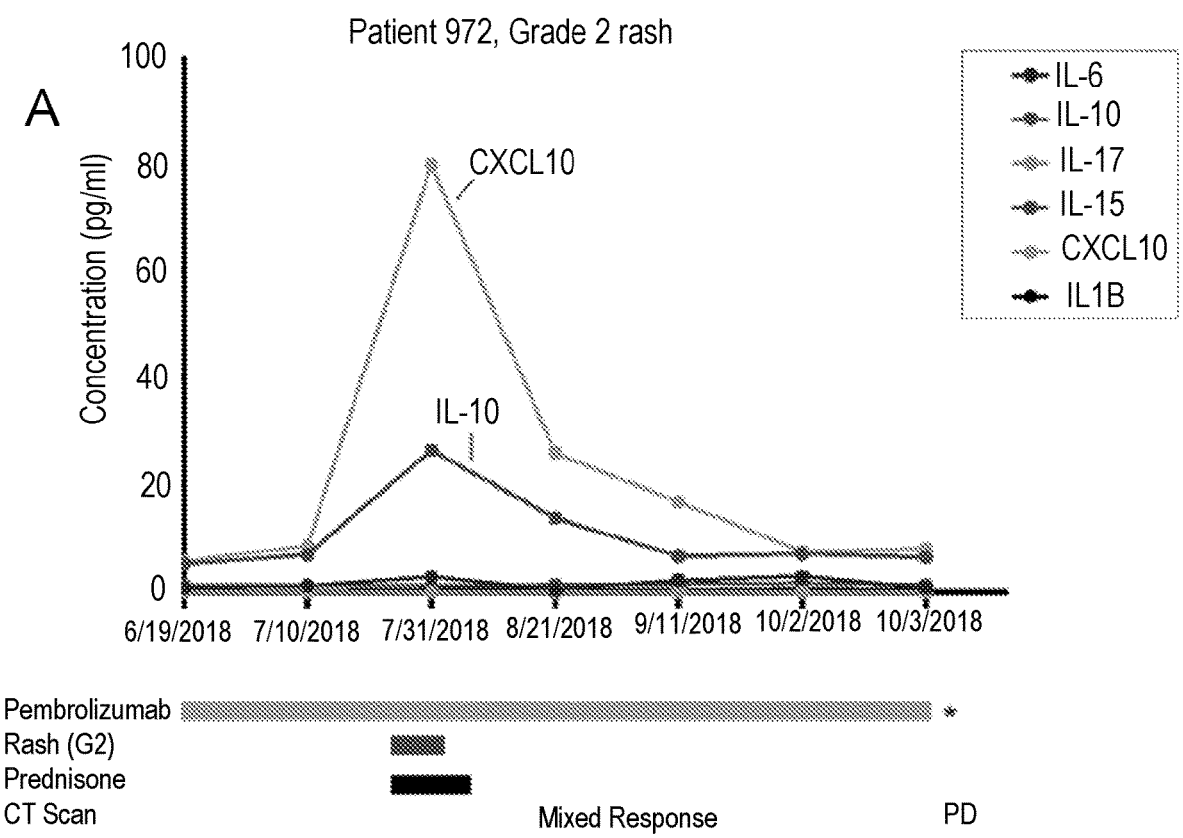
FIGS. 4A-C. Cytokine changes in relation to immune related adverse effects (irAEs). Table summarizing the frequency, severity, and type of irAEs in the pembrolizumab monotherapy and chemoimmunotherapy cohort. The plots reflect concentrations of six cytokines (key, top right) measured at three-week intervals, just prior to each pembrolizumab infusion. The gray bars reflect duration of pembrolizumab treatment, red bars reflect duration of irAEs, black bars reflect steroid treatment, and blue bars reflect antibiotic treatment for infectious complications. Radiologic responses and imaging timepoints are indicated along the bottom.
Figure 4B:
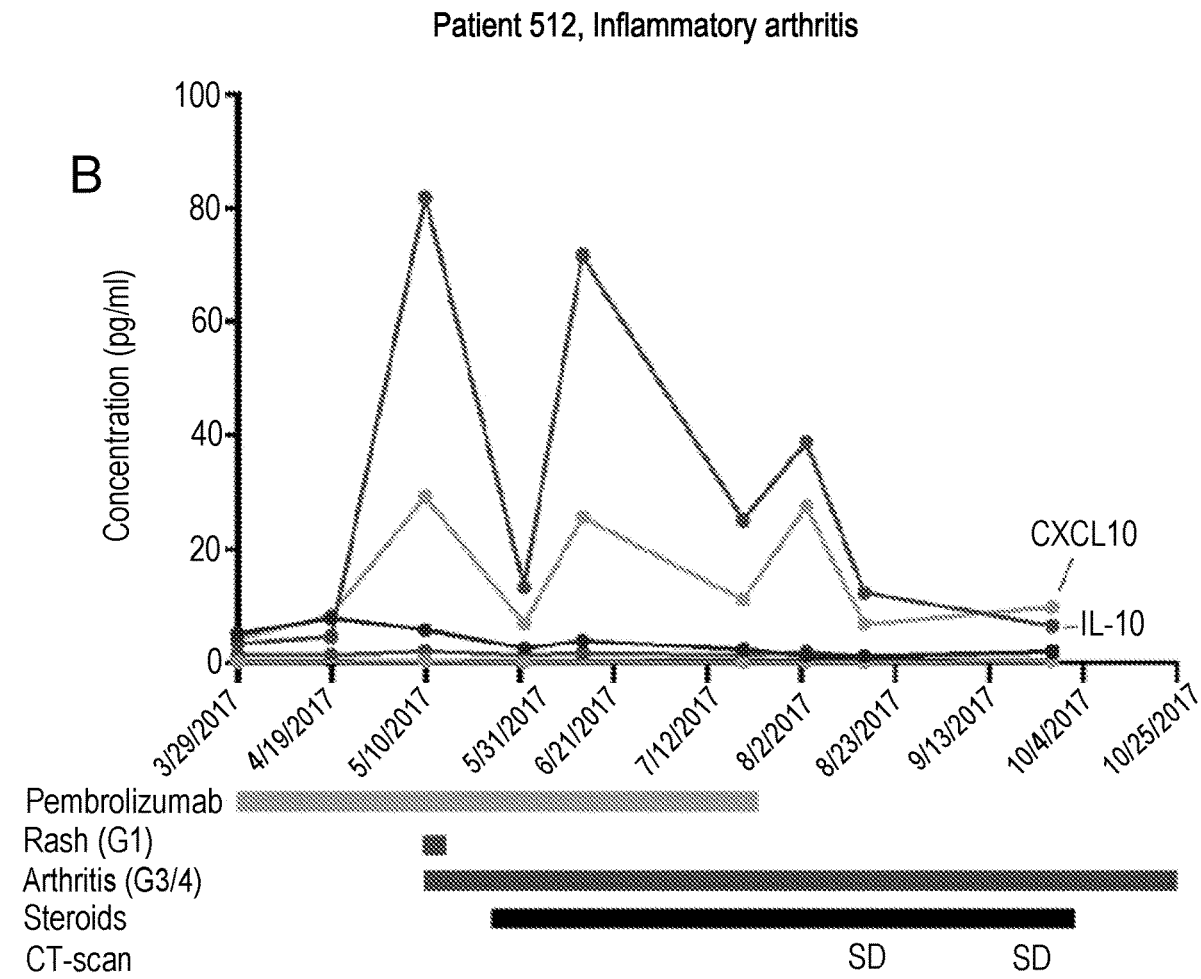
Figure 4C:
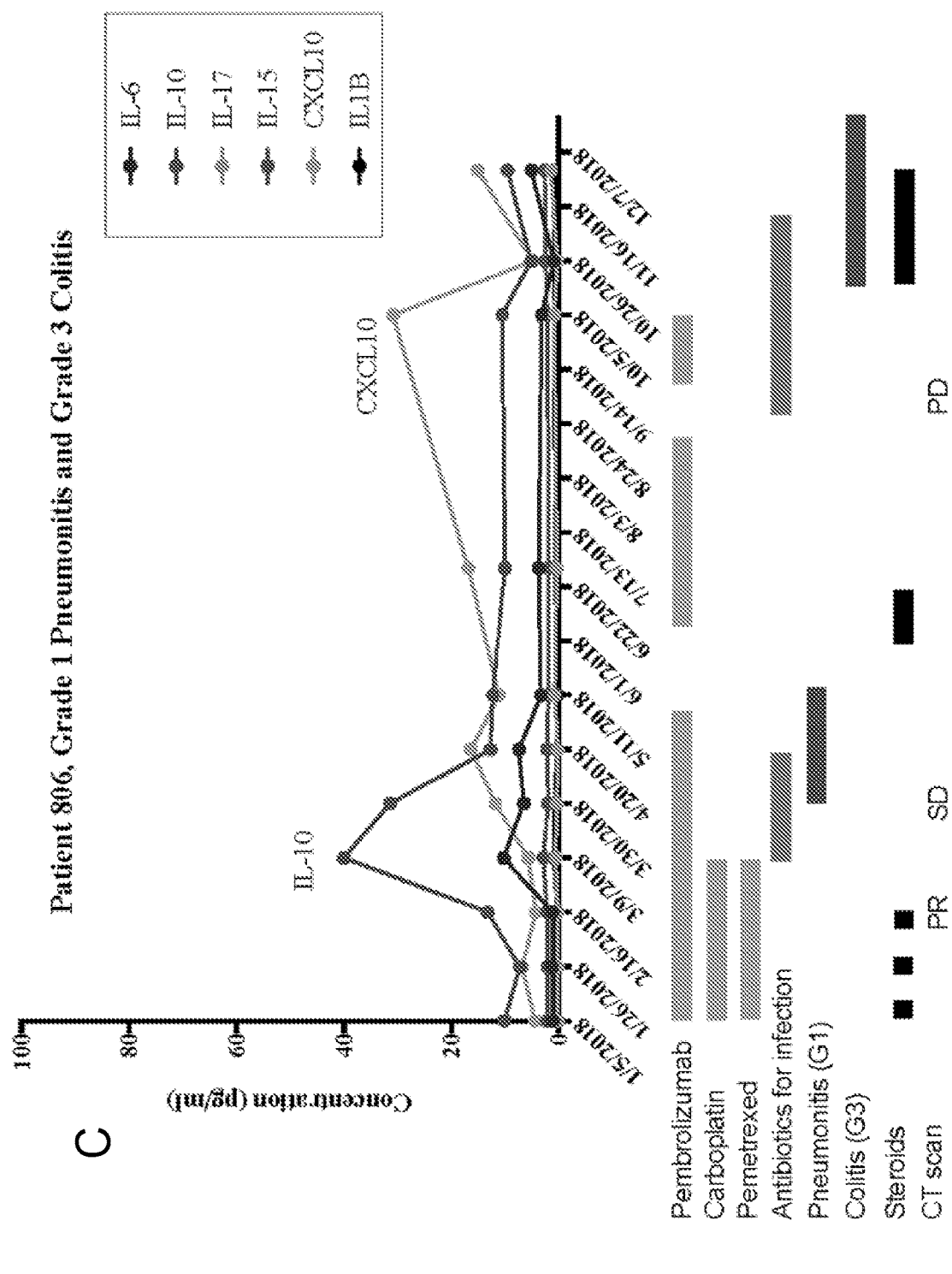
Figure 7B:
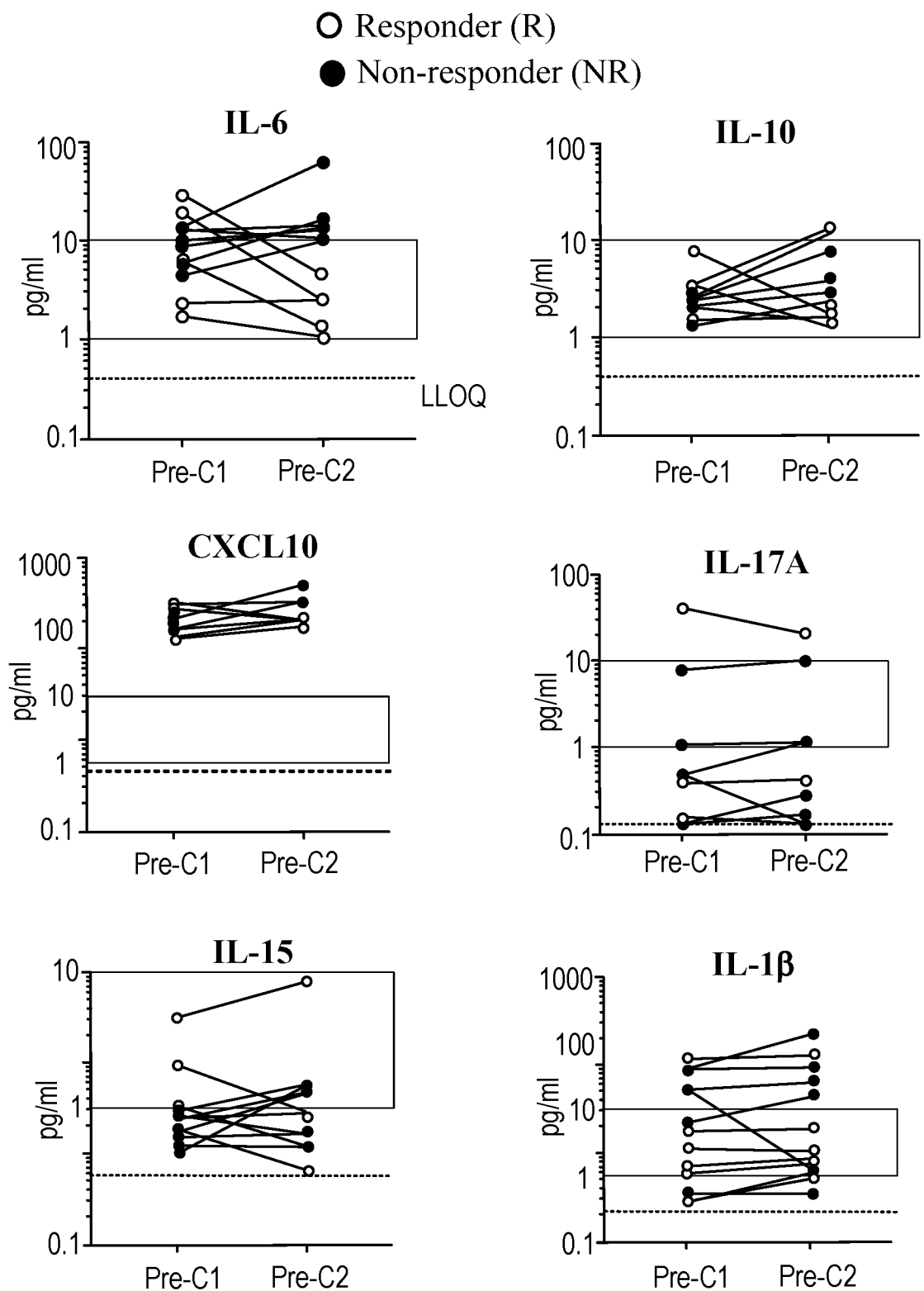
Figure 7C:
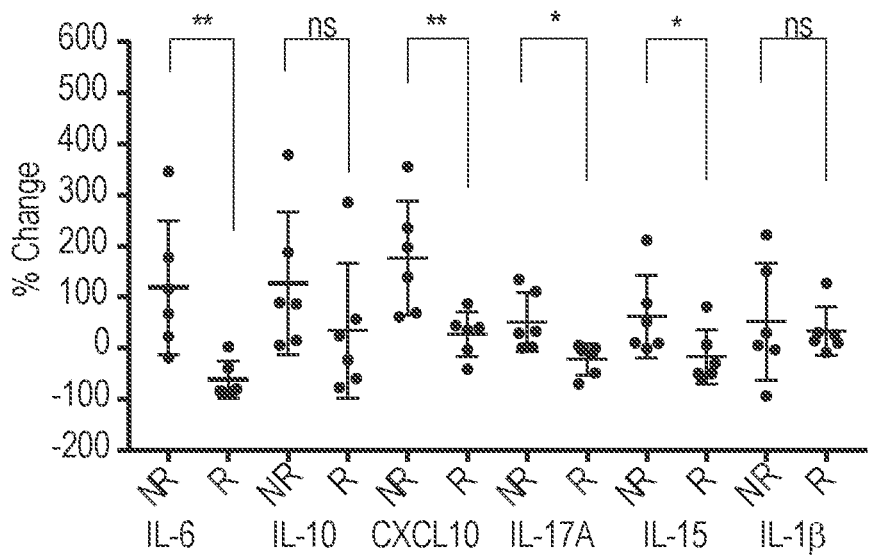
Figure 7C:
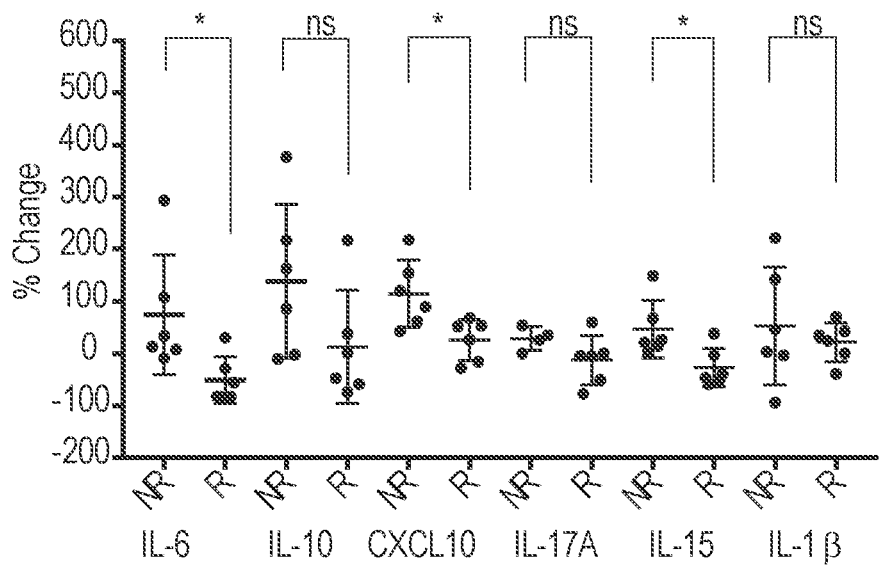
Figure 8:
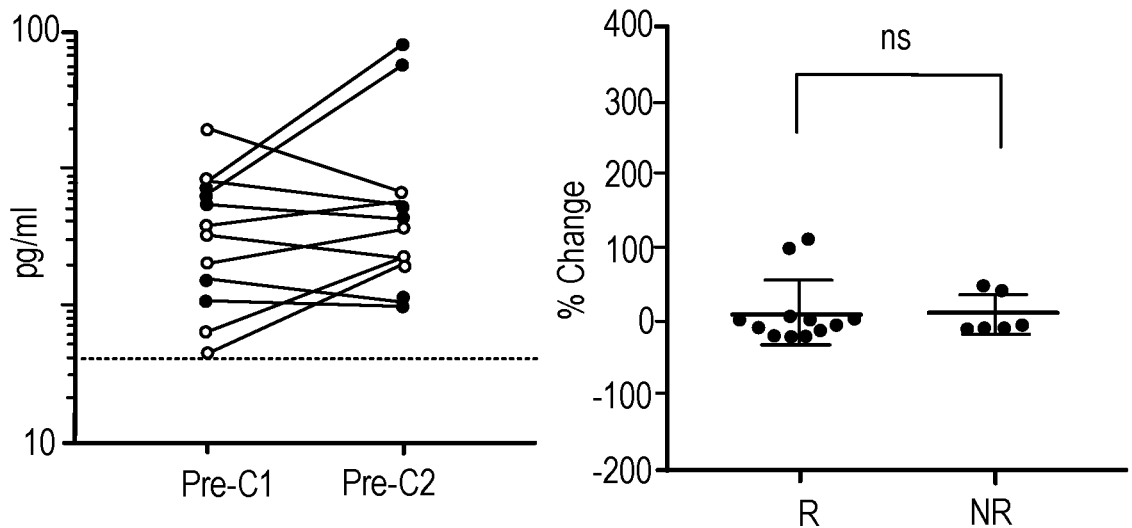
FIG. 8. Cytokine changes in twelve pembrolizumab monotherapy patients with early radiologic responses: clear increase for responders or decrease for nonresponders in tumor burden at first scan and on-treatment timepoints three weeks after first dose of therapy. As in FIGS. 7A-C, except these assays were not carried forward to testing across the entire patient cohort.
Figure 8:
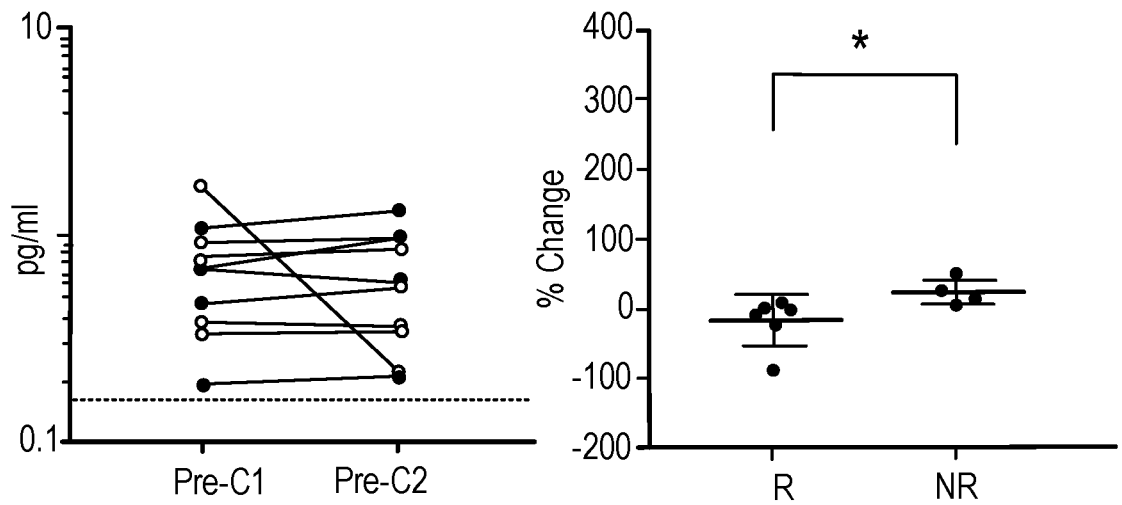
Figure 8:
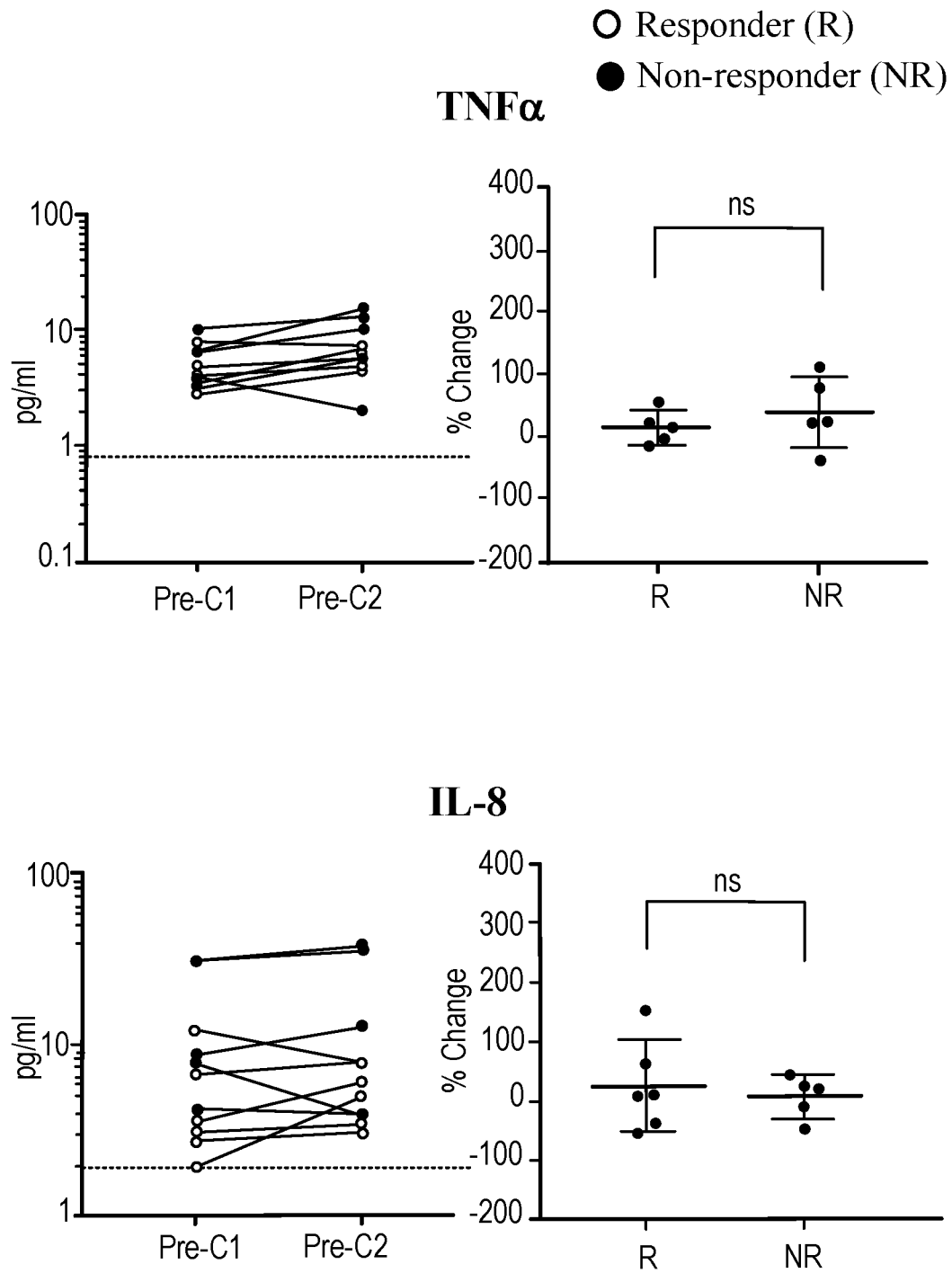
Figure 8:
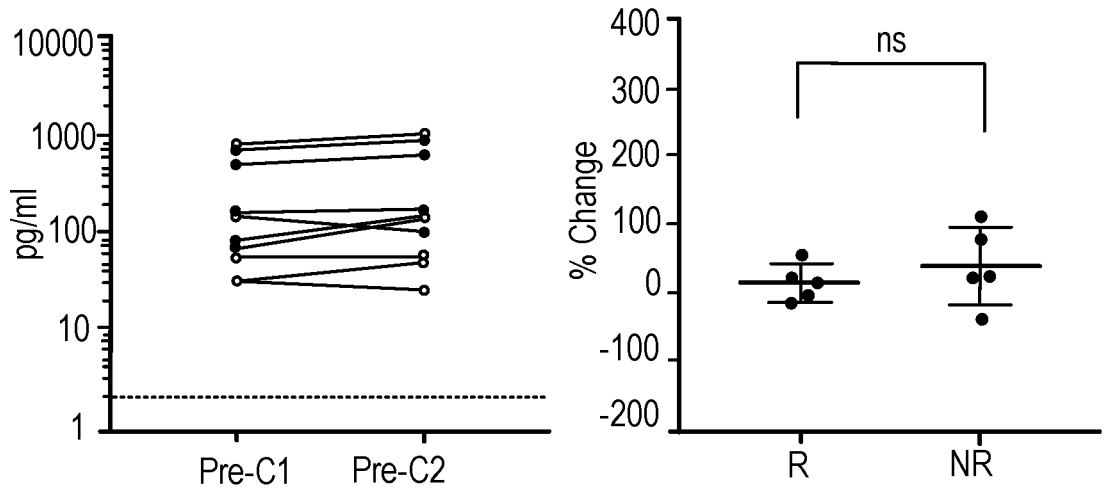
Figure 8:
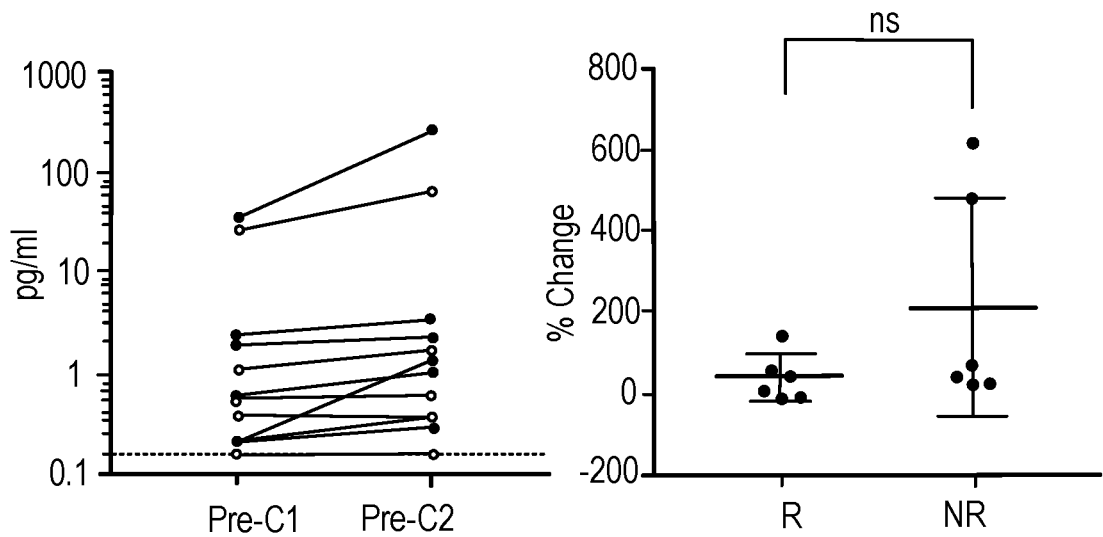

In this cohort, patients had a significantly different PFS according to whether they had decreased, stable, or increased plasma IL-6 concentrations comparing pre- to on-treatment levels (p=0.03, FIG. 2, Table 1). Significant biological variation in IL-6 levels was predetermined as ≥40% change by experimental validation of the sample collection protocol (see further description in Methods). Patients with decreased IL-6 (decreases of more than 40% from pre- to on-treatment timepoints, n=11) had a median PFS of 11 months whereas those with stable (n=21) or increased IL-6 (n=15) had a median PFS of 5 and 4 months, respectively. The distributions of IL-6 changes differed monotherapy patients with partial responses at first scan and on-treatment timepoints three weeks after first dose of therapy (FIG. 7A). All assays had sufficient sensitivity to precisely measure these protein levels in patient plasma (FIGS. 7B and 4). In this patient subset, in addition to IL-6, IL-10, CXCL10, IL-17A, IL-15, and IL-1β increased more in non-responders (FIG. 7C). We extended the analysis to patients with mid-treatment samples available at three weeks after the first dose of pembrolizumab monotherapy or chemimmunotherapy (FIG. 3, including 25 monotherapy patients that were part of the FIG. 2 cohort). IL-6 decreases were observed with and without other cytokine decreases and in patients with both high and low PD-L1 IHC and TMB levels as well as across other disease characteristics (FIG. 4A). IL-6 percentage decrease was not statistically associated with PFS or BOR category in monotherapy (n=25) or chemoimmunotherapy (n=16) treated subgroups of this mixed cohort of limited sample size. None of the other five cytokines (IL-10, CXCL10, IL-17A, IL-15, and IL-1β) demonstrated statistically significant association with clinical responses in this cohort, though more decreases tended to occur in the half of patients with better clinical outcomes for all except IL-1β (FIG. 3A). Because IL-6 directly promotes C-reactive protein (CRP) production in the liver, we measured CRP and found a correlation to the percent change in IL-6 (FIG. 3B) and the relationship to PFS (FIG. 3C) (10). As was observed with IL-6, the pre-treatment levels did not correlate with response (FIG. 3D), however, the quartile of patients with the highest on-treatment CRP levels had shorter PFS (FIG. 3E).

Given the associations of both CRP and IL-6 decreases with patient response, we next explored longitudinal changes in cytokines in relation to clinical appearance of immune-related adverse effects (irAEs). Table 2 summarizes the frequency, severity, and type of irAEs in the pembrolizumab monotherapy and chemoimmunotherapy cohort.

TABLE 2

| Total number of patients | 48 |
|---|---|
| # of iRAEs per patient | |
| 0 | 31 (65%) |
| 1 | 15 (31%) |
| 2 | 2 (4%) |
| # of iRAEs | |
| Grade 1 | 15 |
| Grade 2 | 2 |
| Grade 3 | 2 |
| Grade 4 | 0 |
| Total | 19 |
| Types of iRAEs | |
| Hypothyroidism | 6 |
| Rash | 5 |
| Arthralgia | 3 |
| Hepatitis | 1 |
| AST/ALT increase | 1 |
| Pneumonitis | 1 |
| Colitis | 1 |
| Stomatitis | 1 |

Figure 9:
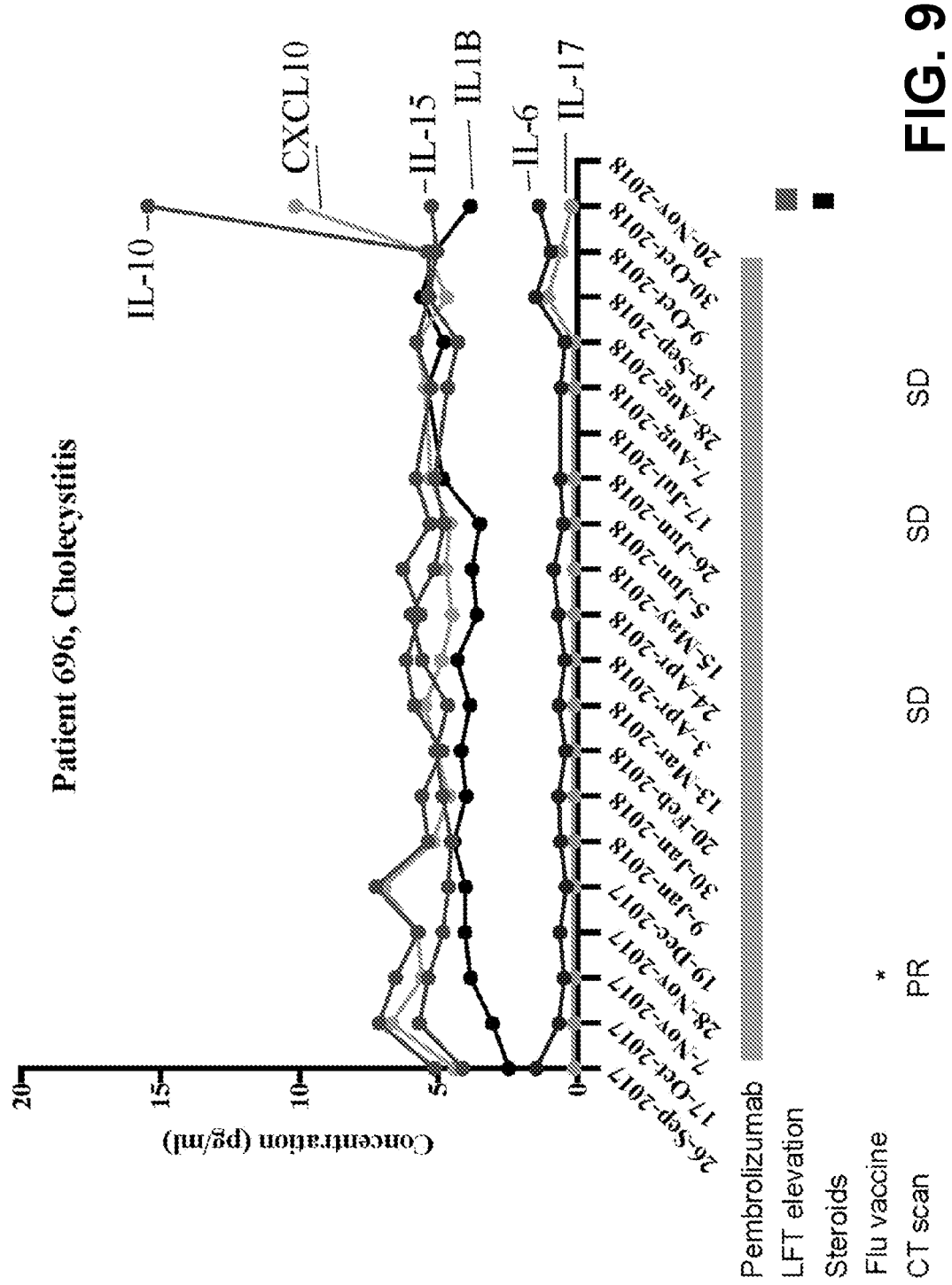
FIG. 9. Cytokine changes in relation to a severe infectious complication. The plots reflect concentrations of six cytokines measured at three-week intervals, prior to each pembrolizumab infusion. Light gray bar reflects duration of pembrolizumab treatment, dark gray bar reflects liver function test elevation measured at onset of abdominal pain, and black bar reflects steroid treatment. Radiologic responses and imaging timepoints are indicated.

We focused on the first-line pembrolizumab monotherapy and chemoimmunotherapy treated cohort (n=48), as they had plasma collected every three weeks while on therapy. At the time of analysis, four of these patients were identified as having grade 2 or 3 irAEs. After the second cycle of therapy, patient 972 developed a rash over 80% body surface area with rapid response to oral steroids and no pembrolizumab treatment delay. The patient had a high peak in CXCL10 and IL-10 levels with return to baseline upon resolution of clinical symptoms. This patient showed a mixed response to therapy on CT scan three weeks after developing the rash and had disease progression approximately four months later. Patient 512 developed an inflammatory polyarthritis leading to cessation of pembrolizumab and showed recurrent peaks in CXCL10 and IL-10 levels. Patient 806 was started on chemi-immunotherapy and developed co-morbid infections as well as a grade 3 colitis leading to pembrolizumab cessation. IL-10 and IL-6 peaks predominated during infectious complications with CXCL10 predominating during colitis flare. Patient 696 was initially misattributed as having an autoimmune hepatitis and was ultimately diagnosed on pathology with cholecystitis (FIG. 9). This patient also demonstrated large peaks in CXCL10 and IL-10 around the time of LFT elevation, illustrating the general role of these cytokine networks in infectious and autoimmune processes.

DISCUSSION

In this study we demonstrated that decreases in plasma IL-6 and CRP are associated with improved outcomes with anti-PD-(L)1 therapy in NSCLC. Decreases are apparent as soon three weeks after the first dose of therapy and also occur with treatment response to combination chemo-immunotherapy. We observed that percent change from baseline was the measure most closely associated to treatment outcomes, likely because of the wide range of physiologic baseline levels across individuals. The enhanced sensitivity of the Simoa platform enabled precise measurement of cytokine changes.

Cytokines are generalized immune-signaling molecules, as illustrated by the four longitudinally monitored patients with cytokines peaks coinciding with immune-related adverse effects and infectious complications. This lack of specificity may dampen cytokine predictive ability as ICB biomarkers, especially in patients with infectious comorbidities, viral disease, vaccination, or other immuno-modulatory therapy. However, since decreases occur after a single dose of therapy, monitoring change in a narrow three-week (or even shorter) window focuses the association to ICB responses. Decreases may also significantly predate radiologic responses. The rapid identification of monotherapy responders could help allocate higher risk therapies such as immunotherapy combinations and other investigational agents to monotherapy nonresponders earlier in the course of their disease.

This clinical association to treatment response raises the question of whether there is a direct link between the IL-6/CRP pathway and the mechanism of PD-1 inhibitors. We sensitively measured eleven plasma cytokines implicated in the immunotherapy response and only IL-6 was associated with response across the cohort. Higher levels of IL-6 and/or CRP have been described as independent risk factors for poor response to PD-1 inhibition in melanoma and triple negative breast cancer[11,12]. In vitro studies have suggested CRP directly interferes with T-cell function (11). IL-6 has immunosuppressive functions and may drive a myeloid compartment that contributes to innate treatment resistance (13). It is also possible that IL-6 directly reflects changes in tumor burden in NSCLC. Previous preclinical studies have shown IL-6 production by lung adenocarcinoma tumor cell lines and positivity in primary tumors (14). In a mouse model of NSCLC responding to PD-1 blockade, IL-6 levels decreased in bronchoalveolar lavage fluid (15). It is possible that a similar mechanism extends to patients and peripheral blood. Another possibility is that decreases in circulation reflect redistribution of inflammatory cells to the TME. The mechanistic possibilities for these observations are numerous. Here, we provide evidence to exclude that the changes in the levels of the solubilized form of the IL-6 receptor underlie the observed changes in levels of IL-6.

In this report, we demonstrated that an ultrasensitive protein assay can predict early response to immunotherapy in NSCLC. Our observation of peripheral blood changes in cytokine levels with ICB response corroborates findings from clinical single-cell studies. By paired single-cell sequencing of T cell receptor and RNA, Yost and colleagues observed a large contribution of anti PD-1-responsive cytotoxic T cells from peripheral blood after treatment, which would not be reflected in a pre-treatment tumor infiltrating lymphocyte assessment (16). Huang and colleagues performed immunoprofiling of peripheral blood T cells and found that the ratio of a re-invigorated phenotype to tumor burden correlated to response (17). Single cell and single molecule studies, such as these, will likely overcome sensitivity boundaries and lead to on-treatment blood-based biomarkers to recognize and improve upon solid tumor ICB responses much earlier in the course of treatment.

REFERENCES

1. Stenken J A, Poschenrieder A J. Bioanalytical chemistry of cytokines—a review. Anal. Chim. Acta 2015; 853:95-115.
2. Topalian S L, Taube J M, Anders R A, Pardoll D M. Mechanism-driven biomarkers to guide immune checkpoint blockade in cancer therapy. Nat. Rev. Cancer 2016; 16(5):275-287.
3. Chen P-L et al. Analysis of Immune Signatures in Longitudinal Tumor Samples Yields Insight into Biomarkers of Response and Mechanisms of Resistance to Immune Checkpoint Blockade. Cancer Discov. 2016; 6(8):827-837.
4. Vilain R E et al. Dynamic Changes in PD-L1 Expression and Immune Infiltrates Early During Treatment Predict Response to PD-1 Blockade in Melanoma. Clin. Cancer Res. Off. J. Am. Assoc. Cancer Res. Clin Cancer Res. 2017 Sep. 1; 23(17):5024-5033
5. Cohen L, Keegan A, Melanson S E F, Walt D R. Impact of clinical sample handling and processing on ultra-low level measurements of plasma cytokines. Clin Biochem. 2019 March; 65:38-44
6. Yeung D et al. Evaluation of highly sensitive immunoassay technologies for quantitative measurements of sub-pg/mL levels of cytokines in human serum. J. Immunol. Methods 2016; 437:53-63.
7. Wu D, Milutinovic M D, Walt D R. Single molecule array (Simoa) assay with optimal antibody pairs for cytokine detection in human serum samples. The Analyst 2015; 140(18):6277-6282.
8. Wu D, Dinh T L, Bausk B P, Walt D R. Long-Term Measurements of Human Inflammatory Cytokines Reveal Complex Baseline Variations between Individuals. Am. J. Pathol. 2017; 187(12):2620-2626.
9. Inter-individual variability and genetic influences on cytokine responses to bacteria and fungi.—PubMed—NCBI [Internet] ncbi.nlm.nih.gov/pubmed/27376574. cited Aug. 21, 2019
10. Rhodes B, Fürnrohr BG, Vyse T J. C-reactive protein in rheumatology: biology and genetics. Nat. Rev. Rheumatol. 2011; 7(5):282-289.
11. Serum I L-6 and CRP as prognostic factors in melanoma patients receiving single agent and combination checkpoint inhibition. |Journal of Clinical Oncology [Internet] ascopubs.org/doi/abs/10.1200/JCO.2019.37.15_suppl.100. cited Aug. 12, 2019
12. Li Y, Fassó M, Emens L A, Molinero L. Abstract CT001: Biomarkers of systemic inflammation associated to reduced clinical activity of atezolizumab monotherapy in patients with metastatic triple negative breast cancer. Cancer Res. 2019; 79 (13 Supplement):CT001-CT001.
13. Chen M-F et al. IL-6-stimulated CD11b+CD14+HLA-DR—myeloid-derived suppressor cells, are associated with progression and poor prognosis in squamous cell carcinoma of the esophagus. Oncotarget 2014; 5(18): 8716-8728.
14. Gao S P et al. Mutations in the EGFR kinase domain mediate STAT3 activation via IL-6 production in human lung adenocarcinomas. J. Clin. Invest. 2007; 117(12): 3846-3856.
15. Akbay E A et al. Interleukin-17A Promotes Lung Tumor Progression through Neutrophil Attraction to Tumor Sites and Mediating Resistance to PD-1 Blockade. J. Thorac. Oncol. Off. Publ. Int. Assoc. Study Lung Cancer 2017; 12(8):1268-1279.
16. Yost K E et al. Clonal replacement of tumor-specific T cells following PD-1 blockade. Nat. Med. [published online ahead of print: Jul. 29, 2019]; doi:10.1038/s41591-019-0522-3
17. Huang A C et al. T-cell invigoration to tumour burden ratio associated with anti-PD-1 response. Nature 2017; 545(7652):60-65.
18. Holland M et al. Separation, banking, and quality control of peripheral blood mononuclear cells from whole blood of melanoma patients. Cell Tissue Bank. [published online ahead of print: Oct. 30, 2018]; doi:10.1007/s10561-018-9734-x
19. Churchman S M, Geiler J, Parmar R, Horner E A, Church L D, Emery P, et al. Multiplexing immunoassays for cytokine detection in the serum of patients with rheumatoid arthritis: lack of sensitivity and interference by rheumatoid factor. Clin Exp Rheumatol. 2012; 30:534-42.
20. Fahey J L, Aziz N, Spritzler J, Plaeger S, Nishanian P, Lathey J L, et al. Need for an External Proficiency Testing Program for Cytokines, Chemokines, and Plasma Markers of Immune Activation. Clin Diagn Lab Immunol. 2000; 7:540-8.
21. Rebelatto M C, Midha A, Mistry A, Sabalos C, Schechter N, Li X, et al. Development of a programmed cell death ligand-1 immunohistochemical assay validated for analysis of non-small cell lung cancer and head and neck squamous cell carcinoma. Diagn Pathol. 2016; 11:95.
22. Tumeh P C, Harview C L, Yearley J H, Shintaku I P, Taylor E J M, Robert L, et al. PD-1 blockade induces responses by inhibiting adaptive immune resistance. Nature. 2014; 515:568-71.
23. Caetano M S, Zhang H, Cumpian A M, Gong L, Unver N, Ostrin E J, et al. IL6 Blockade Reprograms the Lung Tumor Microenvironment to Limit the Development and Progression of K-ras-Mutant Lung Cancer. Cancer Res. 2016; 76:3189-99.
24. Koyama S, Akbay E A, Li Y Y, Herter-Sprie G S, Buczkowski K A, Richards W G, et al. Adaptive resistance to therapeutic PD-1 blockade is associated with upregulation of alternative immune checkpoints. Nat Commun. 2016; 7:10501.
25. Akbay E A, Koyama S, Carretero J, Altabef A, Tchaicha J H, Christensen C L, et al. Activation of the PD-1 pathway contributes to immune escape in EGFR-driven lung tumors. Cancer Discov. 2013; 3:1355-63.
26. Akbay E A, Koyama S, Liu Y, Dries R, Bufe L E, Silkes M, et al. Interleukin-17A Promotes Lung Tumor Progression through Neutrophil Attraction to Tumor Sites and Mediating Resistance to PD-1 Blockade. J Thorac Oncol Off Publ Int Assoc Study Lung Cancer. 2017; 12:1268-79.
27. Duffy, David C., Evan Ferrell, Jeffrey D. Randall, and David R. Walt. Ultra-sensitive Detection of Molecules on Single Molecule Arrays. Quanterix Corp, assignee. U.S. Pat. No. 8,846,415B2. 30 Sep. 2014.

28. Duffy, David C., David M. Rissin, David R. Walt, David Fournier, and Cheuk Kan. Ultra-sensitive Detection of Molecules or Particles Using Beads or Other Capture Objects. Quanterix Corp, assignee. Patent WO2011109364A2.9 Sep. 2011
29. Rissin D M, Walt D R. Digital concentration readout of single enzyme molecules using femtoliter arrays and Poisson statistics. Nano Lett. 2006; 6:520-3.
30. Rissin D M, Walt D R. Digital readout of target binding with attomole detection limits via enzyme amplification in femtoliter arrays. J Am Chem Soc. 2006; 128:6286-7.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
obtaining an initial sample comprising blood from a human subject who has lung cancer; administering to the human subject at least one dose of an antibody that binds to programmed cell death protein 1 (PD-1) or an antibody that binds to programmed cell death 1 ligand 1 (PD-L1);
obtaining a subsequent sample of blood from the human subject;
measuring a level of interleukin 6 (IL-6) in the initial sample and the subsequent sample using an ultrasensitive protein detection technology;
comparing the levels of IL-6 in the initial sample and the subsequent sample; and
(a) administering to the human subject further doses of the antibody if the subsequent sample has decreased levels of IL-6 as compared to the initial sample, or
(b) administering to the human subject at least one therapy with or without further doses of the antibody if the subsequent sample has increased levels or no change in levels of IL-6 as compared to the initial sample.

2. The method of claim 1, wherein the therapy comprises administration of chemotherapy, radiotherapy, chemoradiotherapy, an immunotherapy not comprising the antibody administered in claim 1, and/or anti-angiogenic agents.

3. The method of claim 1, further comprising measuring and comparing the levels of C-reactive protein (CRP) or chemokine (C-X-C motif) ligand 10 (CXCL10) in the initial sample and the subsequent sample.

4. The method of claim 1, further comprising measuring and comparing the levels of CRP; of CRP, interleukin 10 (IL-10), interleukin 15 (IL-15), interleukin 17A (IL-17A), and CXCL10 in the initial sample and the subsequent sample.

5. The method of claim 1, further comprising measuring and comparing the levels of CRP, IL-8, IL-15, IL-17A, IL-2 Receptor alpha, and soluble CD137 in the initial sample and the subsequent sample.

6. The method of claim 1, further comprising measuring and comparing the levels of soluble T cell immunoglobulin-3 (Tim-3), Lymphocyte activation gene-3 (Lag-3), or IL-2 Receptor alpha in the initial sample and the subsequent sample.

7. The method of claim 1, wherein the ultrasensitive protein detection technology is a single molecule array digital ELISA.

8. The method of claim 1, wherein comparing the levels of IL-6 in the initial sample and the subsequent sample comprises determining ratios of the levels of IL-6 in the initial sample and the subsequent sample or determining percentage change between the levels of IL-6 in the initial sample and the subsequent sample.

9. The method of claim 8, further comprising determining an immuno-oncology (I-O) response score using the levels, or ratios or percentage change between the levels of IL-6 in the initial sample and the subsequent sample.

10. The method of claim 9, wherein determining an I-O response score comprises applying principal component analysis or linear regression algorithm.

11. The method of claim 1, wherein the sample comprises plasma or serum.

12. The method of claim 1, wherein the lung cancer is non-small-cell lung cancer (NSCLC).

13. The method of claim 3, further comprising measuring and comparing the levels of one or more of IL-10, IL-15, and IL-17A in the initial sample and the subsequent sample.

14. The method of claim 4, further comprising measuring and comparing the levels of IFNgamma in the initial sample and the subsequent sample.

15. The method of claim 1, wherein the method comprises administering to the human subject at least one dose of an antibody that binds to PD-1.

16. The method of claim 15, wherein the antibody is PF-06801591, AMP-224, BGB-A317, BI 754091, JS001, MEDI0680, PDR001, REGN2810, SHR-1210, TSR-042, pembrolizumab, nivolumab, or pidilizumab.

17. The method of claim 1, wherein the method comprises administering to the human subject at least one dose of an antibody that binds to PD-L1.

18. The method of claim 17, wherein the antibody is BMS-936559, FAZ053, KN035, Atezolizumab, Avelumab, or Durvalumab.

* * * * *